US007060466B2

(12) United States Patent
Weigel et al.

(10) Patent No.: US 7,060,466 B2
(45) Date of Patent: *Jun. 13, 2006

(54) METHODS OF PRODUCING HYALURONIC ACID USING A RECOMBINANT HYALURONAN SYNTHASE GENE

(75) Inventors: Paul H. Weigel, Edmond, OK (US); Paul L. DeAngelis, Edmond, OK (US); Kshama Kumari, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 33 days.

This patent is subject to a terminal disclaimer.

(21) Appl. No.: 11/109,855

(22) Filed: Apr. 20, 2005

(65) Prior Publication Data

US 2005/0202540 A1  Sep. 15, 2005

Related U.S. Application Data

(63) Continuation of application No. 10/011,768, filed on Dec. 11, 2001, which is a continuation of application No. 09/469,200, filed on Dec. 21, 1999, now Pat. No. 6,833,264, which is a continuation of application No. 09/178,851, filed on Oct. 26, 1998, now abandoned, which is a continuation-in-part of application No. 09/146,893, filed on Sep. 3, 1998, now Pat. No. 6,455,304, which is a continuation of application No. 08/270,581, filed on Jul. 1, 1994, now abandoned.

(60) Provisional application No. 60/064,435, filed on Oct. 31, 1997.

(51) Int. Cl.
*C12P 19/26* (2006.01)
*C12P 19/04* (2006.01)

(52) U.S. Cl. .................................. 435/84; 435/101
(58) Field of Classification Search ................. None
See application file for complete search history.

(56) References Cited

U.S. PATENT DOCUMENTS

| | | | |
|---|---|---|---|
| 4,224,179 A | 9/1980 | Schneider | |
| 4,235,871 A | 11/1980 | Papahadjopoulos et al. | |
| 4,511,478 A | 4/1985 | Nowinski et al. | |
| 4,517,295 A | 5/1985 | Bracke et al. | |
| 4,708,861 A | 11/1987 | Popescu et al. | |
| 4,780,414 A | 10/1988 | Nimrod et al. | |
| 4,782,046 A | 11/1988 | Brown et al. | |
| 4,784,990 A | 11/1988 | Nimrod et al. | |
| 4,801,539 A | 1/1989 | Akasaka et al. | |
| 5,015,577 A | 5/1991 | Weigel et al. | |
| 5,023,175 A | 6/1991 | Hosoya et al. | |
| 5,071,751 A | 12/1991 | Morita et al. | |
| 5,948,900 A | 9/1999 | Yother et al. | |
| RE37,336 E | 8/2001 | Weigel et al. | |
| 6,423,514 B1 | 7/2002 | Briskin | |

FOREIGN PATENT DOCUMENTS

| | | |
|---|---|---|
| EP | 0036776 | 5/1988 |
| EP | 0195303 | 11/1989 |
| EP | 0144019 | 6/1990 |
| EP | 0265578 | 7/1993 |
| EP | 0244757 | 11/1994 |
| GB | 2249315 | 5/1992 |
| JP | 62032893 | 2/1987 |
| JP | 63094988 | 4/1988 |
| JP | 02193818 | 3/1992 |
| JP | 4-158796 | 6/1992 |
| WO | 91/03559 | 3/1991 |
| WO | 94/00463 | 1/1994 |
| WO | 95/24497 | 9/1995 |
| WO | 97/20061 | 6/1997 |

OTHER PUBLICATIONS

"The Biosynthesis of Hyaluronic Acid By *Streptococcus*," Stoolmiller, et al., Journal of Biological Chemistry, vol. 244, No. 2, pp. 236-246 (1969).
"Modern Genetics," Ayala, et al. Benjamin/Cummings Publishing Col., Menlo Park CA, p. 45 (1980).
"Strains of *Escherichia coli* Carrying the Structural Gene for Histidyl-tRNA Synthetase on a High Copy-Number Plasmid," Eisenbeis, et al., Mol. Gen. Genet. 183:115-122 (1981).
"Synthesis of Hyaluronate in Differentiated Teratocarcinoma Cells," Prehm et al., J. Biochem, vol. 211, pp. 191-198 (1983).
"Isolation, Structure and Expression of Mammalian Genes for Histidyl-tRNA Synthetase," Tsui, et al., Nucleic Acids Research, vol. 15, No. 8, pp. 3349-3367, (1987).
"Shuttle Vectors Containing a Multiple Cloning Site and a Lacza Gena for Conjugal Transfer of DNA from *Escherichia coli* to Gram-Positive Bacteria," Trieu-Cout, et al., Gene, vol. 102, pp. 99-104, (1991).
"Analysis of TEH Streptococcal Hyaluronic Acid Synthase Complex Using the Photoaffinity Probe 5-Azido-UDP-Glucuronic Acid," Van de Rijn, et al., J. Biol., Chem., vol. 267, No. 34, pp. 24302-24306, (1992).
"Molecular Characterization of a Locus Required for Hyaluronic Acid Capsule Production in Group A *Streptococci*," Dougherty, et al., J. Exp. Med., vol. 175, pp. 1291-1299, (1992).

(Continued)

*Primary Examiner*—Robert A. Wax
(74) *Attorney, Agent, or Firm*—Dunlap, Codding & Rogers, P.C.

(57) ABSTRACT

The present invention relates to a nucleic acid segment having a coding region segment encoding enzymatically active *Streptococcus equisimilis* hyaluronate synthase (seHAS), and to the use of this nucleic acid segment in the preparation of recombinant cells which produce hyaluronate synthase and its hyaluronic acid product. Hyaluronate is also known as hyaluronic acid or hyaluronan.

20 Claims, 15 Drawing Sheets

OTHER PUBLICATIONS

"HYALURONAN," Laurent, et al., FASEB Journal, vol. 6, pp. 2397-2404, (1992).

"Isolation of a *Streptococcus pyogenes* Gene Locus That Directs Hyaluronan Biosynthesis in Acapsular Mutants and in Heterologous Bacteria," DeAngelis, et al., J. Biol. Chem., vol. 268, No. 20, pp. 14568-14571, (1993).

"Hyaluronate Synthase: Cloning and Sequencing of the Gene from *Streptococcus* SP.," Lansing, et al., J. Biochem., vol. 289, pp. 179-184, (1993).

"Molecular Characterization of HASB from an Operon Required for Hyaluronic Acid Synthesis in Group A *Streptococci*," Dougherty, et al., J. Biol. Chem., vol. 268, No. 10, pp. 7118-7121, (1993).

"Molecular Cloning, Identification, and Sequence of the Hyaluronan Synthase Gene from Group A *Streptococcus* Pyogenes," DeAngelis, et al., J. Biol. Chem., vol. 268, No. 26, pp. 19181-19184, (1993).

"Molecular Characterization of HASA from an Operon Required for Hyaluronic Acid Synthesis in Group A *Streptococci*," Dougherty, et al., J. Biol. Chem., vol. 269, No. 1, pp. 169-175, (1994).

"The *Streptococcus* Pyogenes Hyaluronan Sytnhase: Sequence Comparison and Conservation Among Various Group A Strains," DeAngelis, et al., Biochem. and Biophy. Res. Comm., vol. 199, No. 1, pp. 1-10, (1994).

"The Production of Capsules, Hyaluronic Acid and Hyaluronidase by Group A and Group C *Streptococci*", MacLennan, J. Gen. Microbiol., 14:134-142 (1956).

"The Isolation and Characterization of a Hyaluronidase Produced by a Capsulated Strain of Group C *Streptococcus*", MacLennan, J. Gen. Microbiol., 14:143-152 (1956).

"The Biosynthesis of Hyaluronic Acid by Group A *Streptococcus*", Markovitz et al., J. Biol. Chem., 234 (9):2343-2350 (1959).

"Biosynthesis of Hyaluronic Acid by *Streptococcus*", Sugahara et al., J. Biol. Chem., 254:6252-6261 (1979).

"Streptococcal Hyaluronic Acid: Proposed Mechanisms of Degradation and Loss of Synthesis During Stationary Phase", Van de Rijn, J. Bacteriol., 156(3): 1059-1065 (1983).

"Solubilization of Hyaluronic Acid Synthetic Activity From *Streptococci* and its Activation with Phospholipids", Triscott et al., J. Biol. Chem., 261 (13):6004-6009 (1986).

"Isolation of Streptococcal Hyaluronate Synthase", Prehm et al., Biochem. J., 235:887-889 (1986).

"Streptococcal Hyaluronic Acid; Proposed Mechanisms of Degradation and Loss of Synthesis During Stationary Phase", Van de Rijn, J. Bacteriol., 156(3):1059-1065 (1983).

"Homologs of the Xenopus Developmental Gene DG42 are Present in Zebrafish and Mouse and are Involved in the Synthesis of Nod-Like Chitin Oligosaccharides During Early Embryogenesis", Semino et al., Proc. Natl Acad. Sci. USA, 93:4548-4553 (1996).

"Enzymological Characterization of the Pasteurella Multocida Hyaluronic Acid Synthase", DeAngelis, Biochemistry, 35 (30): 9768-9771 (1996).

"Molecular Cloning, Expression, and Characterization of the Authentic Hyaluronan Synthase from Group C *Streptococcus equisimilis*", Kumari and Weigel, J. Biol. Chem., 272(51): 32539-32546 (1997).

"Hyaluronan Synthases", Weigel et al., J. Bil. Chem., 272 (22): 13997-14000 (1997).

"Identification and Molecular Cloning of a Unique Hyaluronan Synthase from Pasteurella Multocida", DeAngelis et al., J. Biol. Chem., 273(14): 8454-8458 (1998).

"The Role of the Mucoid Polysaccharide (Hyaluronic Acid) in the Virulence of Group A Hemolytic *Streptococci*", Kass et al., J. Of Exp. Med., 79:319-330 (1944).

"The Biology of Hyaluronan", Evered and Whelan Eds., CIBA Foundation Symposium 143 (1989).

"Hyaluronic Acid Capsule is a Virulence Factor for Mucoid Group A *Streptococci*", Wessels et al., Microbiology, 88:8317-8321 (1991).

"New Frontiers in Medical Sciences: Redefining Hyaluronan", Abatangelo and Weigel Eds., (2000).

```
cvHAS  MG--KNIIIM VSWYTIITS- ---------- ---------NL IAVGGASLI  APAITG VLH   39
seHAS  MRTLKNLIT- ---------- ---------- ---------V VAFSIEWVL  I-----  VNV   25
spHAS  VPIFKKTLI- ---------- ---------- ---------V LSFIFLISI  I-----  LNM   25
huHAS  MHCERFLCIL RI---IGTTL ---------- ---------- ----FGVSL  LGITAA  IVG   33
xlHAS  MK-EKAAETM EIPEGIPKDL EPKHPTLWRI IYYSFGVVL  ATITAA  VAE   49 cvHAS  WNIALST--I WGVSA  IFV FGFFLAQVLF SELNRKRLRK WISLRPKGWN         87
seHAS  YLFGAKG--- -SLSI  FLL IAYLLVKMSL SFF-YKPFKG R---AGQ--Y         65
spHAS  YLFGT-S--- -TVGI  VIL ITYLVIKLGL SFL-YEPFKG N---PHD--Y         64
huHAS  YQFIQTDNYY FSFGL  AFL ASHLIIQSLF AFLEHRKMKK SLETPIK--L         81
xlHAS  FQVLKHEAIL FSLGL  LAM LLHLMMQSLF AFLEIRRVNK S-ELPCS--F         96 cvHAS  DVRL VI  AG  R DPYMFQK C  ES VRDSD  GNVA-RLIC  I  DEDDDMR  136
seHAS  K-- AT PS  N  DAESLLE T  KS VQQQT  PLAE--IYV  D  SADETGI  111
spHAS  K-- AV PS  N  DAESLLE T  KS VLAQT  PLSE--IYI  D  SSNTDAI  110
huHAS  NKTV L C AA   DPDYLRK C  Q  VKRLT  PG--IKVVM  I  NSEDDLY  129
xlHAS  KKTV L T AG   NPEYLIK C  ES CKYVK  PKDKLKIIL  I  NTEDDAY  146 cvHAS  MAAVYKAIYN DN-------- ---------- -------IKKPE ---------FV LCESDDKEGE  165
seHAS  KR-------- ---------- ---IEDYVRD ---------- TGDLSSNVIV HRSEKNQGKR  140
spHAS  QL-------- ---------- ---IEEYVNR ---------- EVDICRNVIV HRSLVNKGKR  139
huHAS  MMDIFSEVMG RDKSATYIWK NNFHE-KGPG ETDES----- -------HKESS SKPLNEDEGI  168
xlHAS  MMEMFKDVFH GEDVGTYVWK GNYHTVKKPE ETNKGSCPEV SKPLNEDEGI              196 cvHAS  RIDSDF---S RDICVL PHR GKRECLYTG  QLAKMDPSVN AVVLI DS  V  212
seHAS  HA-------- --   AW- ---------- -A-------- FLTV- DS  Y  163
spHAS  HA-------- --   AW- ---------- -A-------- FLTV- DS  Y  162
huHAS  QHVTQLVLSN KSICIM KWG GKREVMYTA  R--ALGRSVD YVQVC DS  M  216
xlHAS  NMVEELVRNK RCVCIM QWG GKREVMYTA  Q--AIGTSVD YVQVC DS  K  244
```

Fig. 2

```
cvHAS    LEKDAILEVV  YPLACDPEIQ  AVAGECKIWN  T-DTLLSLLV  AWRMYSATCV  261
seHAS    IYPDALELLL  KTFNDPTVFA  ATG-HLNVRI  RQTNLLTRLT  DIRYDNAFGV  212
spHAS    IYPNALELLL  KSFNDETVYA  ATG-HLNARI  RQTNLLTRLT  DIRYDNAIGV  211
huHAS    LDPASSVIMV  KVLEEDPMVG  GVGGDVQILN  KYDSWISFLS  SVRYWMAFNI  266
xlHAS    LDELATVIMV  KVLESNDMYG  AVGGDVRILN  PYDSFISFMS  SLRYWMAHNV  294 cvHAS    LRSACOFFRT  VQCVCGPLGA  KIDIKEIK    DPWISGRLIG  QKCTYGDDR   311
seHAS    TRAAOSVTGN  ILVCSGPLSV  RREVVVPNI   DRYINQTLG   IPVSIGDDRC  262
spHAS    RAAOSLTGN   ILVCSGPLSI  RREVIIPNL   ERYKNOTLG   LPVSIGDDRC  261
huHAS    RACOYFGC    VQCISGPLGM  RNSLLHEFV   EDWYNOEMCG  NQCSFGDDRH  316
xlHAS    RACOYFDC    VSCISGPLGM  RNNILQVFL   EAWYROKLG   TYCTLGDDRH  344 cvHAS    NEILMRGK    KVVFTPFAVG  WSDSFTNVFR  YIVOTRWSN   WCREIWYTL   361
seHAS    TNYATDLG-   RTVYQSTAKC  ITDVFDKMST  YLKONRMN    FFRHSIISV   311
spHAS    NYAIDLG-    RTVYQSTARC  DTDVFQLKS   YLKONRWNK   FFRHSIISV   310
huHAS    RVLSLDY     ATKYTARSKC  LTETFIEYLR  WLNOTRWSK   YFREWLYNA   366
xlHAS    RVLSMOY     RTKYTHKSRA  FSETDSLYLR  WLNOTRMTN   YFRIEWLYNA  394 cvHAS    FAAWKHGLSG  IDLAFCLYQ   ITYFFLVIYL  FSRLAVEADP  RAQTATVIVS  411
seHAS    KKIMNNPFVA  LETILIVSMF  MMLVYSVVDF  FVGNVREFDW  LRVLAFLVII  361
spHAS    KKILSNPIVA  LGTIFIVVMF  MMLIVAIGNL  LENQAIQLDL  IKLFAFLSII  360
huHAS    MWFHKHH---  IMMTYIAIIT  GEFPFFLIAT  VIQLFYRGKI  WNILLFLLTV  413
xlHAS    QWWHKHH---  IMMTYISVVS  FIFPFFITAT  VIRLIYAGTI  WNVVWLLLCI  441 cvHAS    TTVAIKCGY   FSFRAKDIRA  FYFV-LTFV   YEFFCMIHARI TAMMLWDIG   460
seHAS    FIVALCRNIH  YM--LKHPLS  FLLSPFGVL   HLFVLQLKL   YSLFIRNAD   409
spHAS    FIVALCRNIH  YM--VKHPAS  FLLSPLGIL   HLFVLQLKL   YSLCIKNTE   408
huHAS    QLVGLIKSS-  FASCLRGNIV  MVFMSLSVL   YMSSLLAKM   FAIAINKAG   462
xlHAS    QIMSLFKSI-  YACWLRGNFI  MLLMSLSML   YMTGLLSKY   FALILNKTG   490
```

Fig. 2

```
cvHAS   WDRGGNEKP SVGTRVALWA KQYLIAYMWW AAVVGAGVYS IVHNWMFDWN     510
seHAS   G----R-K-K L--------- ---------- ---------- -L*            417
spHAS   G----R-K-K V--------- ---------- --------T- IFK*           419
huHAS   G----R-T-T IVVNFIGL-- ---IPVSVWF TILLGGVIFT IYKESKRPFS     505
xlHAS   G----R-K-K IVGNYMPI-- ---LPLSIWA AVLCGGVGYS IYMDCQNDWS     533 cvHAS   S-----LSYR FALVGIC-SY IVFIVIVLVV YFTGKITTWN FTKLQKELIE     554
huHAS   ES-KQTVLIV GTLLYAC--- --YWVMLLTL YV---VLINK CGRRKKGQQY     546
xlHAS   TPEKQKEMY- -HLLYGCVGY VMYWVIMAVM YW---VWVKR CCR-KRSQTV     577 cvHAS   DRVLYDATTN AQSV*                                           568
huHAS   DMVL-----DV*                                               552
xlHAS   TLVH----DI PDMCV*                                          588
```

Fig. 2

SEQUENCE LISTING

```
<160> NUMBER OF SEQ ID NOS: 10

<210> SEQ ID NO 1
<211> LENGTH: 1254
<212> TYPE: DNA
<213> ORGANISM: Streptococcus equisimilis

<400> SEQUENCE: 1
atgagaacat taaaaaacct cataactgtt gtggccttta gtattttttg ggtactgttg      60
atttacgtca atgtttatct cttttggtgct aaaggaagct tgtcaattta tggcttttg    120 ctgatagctt acctattagt caaaatgtcc ttatccttttt tttacaagcc atttaaggga   180
agggctgggc aatataaggt tgcagccatt attccctctt ataacgaaga tgctgagtca   240
ttgctagaga cctttaaaaag tgttcagcag caaacctatc ccctagcaga aatttatgtt    300
gttgacgatg gaagtgctga tgagacaggt attaagcgca ttgaagacta tgtgcgtgac    360
actggtgacc tatcaagcaa tgtcattgtt catcggtcag agaaaaatca aggaaagcgt    420
catgcacagg cctgggcctt tgaaagatca gacgctgatg tcttttttgac cgttgactca    480 gatacttata tctaccctga tgctttagag gagttgttaa aaaccttttaa tgacccaact    540 gttttttgctg cgacgggtca ccttaatgtc agaaatagac aaaccaatct cttaacacgc    600
ttgacagata ttcgctatga taatgctttt ggcgttgaac gagctgccca atccgttaca    660
ggtaatatcc ttgtttgctc aggtccgctt agcgtttaca gacgcgaggt ggttgttcct    720
aacatagata gatacatcaa ccagaccttc ctgggtattc ctgtaagtat tggtgatgac    780
aggtgcttga ccaactatgc aactgattta ggaaagactg tttatcaatc cactgctaaa    840
tgtattacag atgttcctga caagatgtct acttacttga agcagcaaaa ccgctggaac    900
aagtccttct ttagagagtc cattatttct gttaagaaaa tcatgaacaa tccttttgta    960
gccctatgga ccatacttga ggtgtctatg tttatgatgc ttgtttattc tgtggtggat   1020
ttctttgtag gcaatgtcag agaatttgat tggctcaggg ttttagcctt tctggtgatt   1080
atcttcattg ttgccctgtg tcggaacatt cattacatgc ttaagcaccc gctgtccttc   1140
```

```
ttgttatctc cgttttatgg ggtgctgcat ttgtttgtcc tacagccctt gaaattatat    1200 tctctttta  ctattagaaa tgctgactgg ggaacacgta aaaaattatt ataa          1254
```

<210> SEQ ID NO 2
<211> LENGTH: 417
<212> TYPE: PRT
<213> ORGANISM: Streptococcus Equisimilis

<400> SEQUENCE: 2

| | | | | | | | | | | | | | | |
|---|---|---|---|---|---|---|---|---|---|---|---|---|---|---|
| Met | Arg | Thr | Leu | Lys | Asn | Leu | Ile | Thr | Val | Val | Ala | Phe | Ser | Ile | Phe |
| 1 | | | | 5 | | | | | 10 | | | | | 15 | |
| Trp | Val | Leu | Leu | Ile | Tyr | Val | Asn | Val | Tyr | Leu | Phe | Gly | Ala | Lys | Gly |
| | | | 20 | | | | | 25 | | | | | 30 | | |
| Ser | Leu | Ser | Ile | Tyr | Gly | Phe | Leu | Leu | Ile | Ala | Tyr | Leu | Leu | Val | Lys |
| | | 35 | | | | | 40 | | | | | 45 | | | |
| Met | Ser | Leu | Ser | Phe | Phe | Tyr | Lys | Pro | Phe | Lys | Gly | Arg | Ala | Gly | Gln |
| | 50 | | | | | 55 | | | | | 60 | | | | |
| Tyr | Lys | Val | Ala | Ala | Ile | Ile | Pro | Ser | Tyr | Asn | Glu | Asp | Ala | Glu | Ser |
| 65 | | | | | 70 | | | | | 75 | | | | | 80 |
| Leu | Leu | Glu | Thr | Leu | Lys | Ser | Val | Gln | Gln | Gln | Thr | Tyr | Pro | Leu | Ala |
| | | | | 85 | | | | | 90 | | | | | 95 | |
| Glu | Ile | Tyr | Val | Val | Asp | Asp | Gly | Ser | Ala | Asp | Glu | Thr | Gly | Ile | Lys |
| | | | 100 | | | | | 105 | | | | | 110 | | |
| Arg | Ile | Glu | Asp | Tyr | Val | Arg | Asp | Thr | Gly | Asp | Leu | Ser | Ser | Asn | Val |
| | | 115 | | | | | 120 | | | | | 125 | | | |
| Ile | Val | His | Arg | Ser | Glu | Lys | Asn | Gln | Gly | Lys | Arg | His | Ala | Gln | Ala |
| | 130 | | | | | 135 | | | | | 140 | | | | |
| Trp | Ala | Phe | Glu | Arg | Ser | Asp | Ala | Asp | Val | Phe | Leu | Thr | Val | Asp | Ser |
| 145 | | | | | 150 | | | | | 155 | | | | | 160 |
| Asp | Thr | Tyr | Ile | Tyr | Pro | Asp | Ala | Leu | Glu | Glu | Leu | Leu | Lys | Thr | Phe |
| | | | | 165 | | | | | 170 | | | | | 175 | |
| Asn | Asp | Pro | Thr | Val | Phe | Ala | Ala | Thr | Gly | His | Leu | Asn | Val | Arg | Asn |
| | | | 180 | | | | | 185 | | | | | 190 | | |
| Arg | Gln | Thr | Asn | Leu | Leu | Thr | Arg | Leu | Thr | Asp | Ile | Arg | Tyr | Asp | Asn |
| | | 195 | | | | | 200 | | | | | 205 | | | |
| Ala | Phe | Gly | Val | Glu | Arg | Ala | Ala | Gln | Ser | Val | Thr | Gly | Asn | Ile | Leu |
| | 210 | | | | | 215 | | | | | 220 | | | | |
| Val | Cys | Ser | Gly | Pro | Leu | Ser | Val | Tyr | Arg | Arg | Glu | Val | Val | Val | Pro |
| 225 | | | | | 230 | | | | | 235 | | | | | 240 |
| Asn | Ile | Asp | Arg | Tyr | Ile | Asn | Gln | Thr | Phe | Leu | Gly | Ile | Pro | Val | Ser |
| | | | | 245 | | | | | 250 | | | | | 255 | |
| Ile | Gly | Asp | Asp | Arg | Cys | Leu | Thr | Asn | Tyr | Ala | Thr | Asp | Leu | Gly | Lys |
| | | | 260 | | | | | 265 | | | | | 270 | | |
| Thr | Val | Tyr | Gln | Ser | Thr | Ala | Lys | Cys | Ile | Thr | Asp | Val | Pro | Asp | Lys |
| | | 275 | | | | | 280 | | | | | 285 | | | |
| Met | Ser | Thr | Tyr | Leu | Lys | Gln | Gln | Asn | Arg | Trp | Asn | Lys | Ser | Phe | Phe |
| | 290 | | | | | 295 | | | | | 300 | | | | |
| Arg | Glu | Ser | Ile | Ile | Ser | Val | Lys | Lys | Ile | Met | Asn | Asn | Pro | Phe | Val |
| 305 | | | | | 310 | | | | | 315 | | | | | 320 |
| Ala | Leu | Trp | Thr | Ile | Leu | Glu | Val | Ser | Met | Phe | Met | Met | Leu | Val | Tyr |
| | | | | 325 | | | | | 330 | | | | | 335 | |
| Ser | Val | Val | Asp | Phe | Phe | Val | Gly | Asn | Val | Arg | Glu | Phe | Asp | Trp | Leu |
| | | | 340 | | | | | 345 | | | | | 350 | | |
| Arg | Val | Leu | Ala | Phe | Leu | Val | Ile | Ile | Phe | Ile | Val | Ala | Leu | Cys | Arg |

-continued

```
                355                 360                 365
Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu

<210> SEQ ID NO 3
<211> LENGTH: 22
<212> TYPE: DNA
<213> ORGANISM: Artificial Sequence
<220> FEATURE:
<223> OTHER INFORMATION: Primer se1

<400> SEQUENCE: 3
gctgatgaga caggtattaa gc                                          22

<210> SEQ ID NO 4
<211> LENGTH: 20
<212> TYPE: DNA
<213> ORGANISM: Artificial sequence
<220> FEATURE:
<223> OTHER INFORMATION: Primer se2

<400> SEQUENCE: 4
atcaaattct ctgacattgc                                             20

<210> SEQ ID NO 5
<211> LENGTH: 20
<212> TYPE: DNA
<213> ORGANISM: Artificial sequence
<220> FEATURE:
<223> OTHER INFORMATION: Primer sesp1

<400> SEQUENCE: 5
gactcagata cttatatcta                                             20

<210> SEQ ID NO 6
<211> LENGTH: 17
<212> TYPE: DNA
<213> ORGANISM: Artificial sequence
<220> FEATURE:
<223> OTHER INFORMATION: Primer sesp2

<400> SEQUENCE: 6
tttttacgtg ttcccca                                                17

<210> SEQ ID NO 7
<211> LENGTH: 1740
<212> TYPE: DNA
<213> ORGANISM: Paramecium bursaria chlorella virus

<400> SEQUENCE: 7
aagacttctt gaaagttaca atgggtaaaa atataatcat aatggtttcg tggtacacca    60
tcataacttc aaatctaatc gcggttggag gagcctctct aatcttggct ccggcaatta   120
ctgggtatgt tctacattgg aatattgctc tctcgacaat ctggggagta tcagcttatg   180
gtattttcgt ttttgggttt ttccttgcac aagtttttatt ttcagaactg aacaggaaac   240
gtcttcgcaa gtggatttct ctcagaccta agggttggaa tgatgttcgt ttggctgtga   300
```

-continued

```
tcattgctgg atatcgcgag gatccttata tgttccagaa gtgcctcgag tctgtacgtg    360
actctgatta tggcaacgtt gcccgtctga tttgtgtgat tgacggtgat gaggacgatg    420
atatgaggat ggctgccgtt tacaaggcga tctacaatga taatatcaag aagcccgagt    480
ttgttctgtg tgagtcagac gacaaggaag gtgaacgcat cgactctgat ttctctcgcg    540
acatttgtgt cctccagcct catcgtggaa aacgggagtg tctttatact gggtttcaac    600
ttgcaaagat ggaccccagt gtcaatgctg tcgttctgat tgacagcgat accgttctcg    660
agaaggatgc tattctggaa gttgtatacc cacttgcatg cgatcccgag atccaagccg    720
ttgcaggtga gtgtaagatt tggaacacag acactctttt gagtcttctc gtcgcttggc    780
ggtactattc tgcgttttgt gtggagagga gtgcccagtc tttttcagg actgttcagt    840
gcgttggggg gccactgggt gcctacaaga ttgatatcat taaggagatt aaggacccct    900
ggatttccca gcgctttctt ggtcagaagt gtacttacgg tgacgaccgc cggctaacca    960
acgagatctt gatgcgtggt aaaaaggttg tgttcactcc atttgctgtt ggttggtctg   1020
acagtccgac caatgtgttt cggtacatcg ttcagcagac ccgctggagt aagtcgtggt   1080
gccgcgaaat ttggtacacc ctcttcgccg cgtggaagca cggtttgtct ggaatttggc   1140
tggcctttga atgtttgtat caaattacat acttcttcct cgtgatttac ctcttttctc   1200
gcctagccgt tgaggccgac cctcgcgccc agacagccac ggtgattgtg agcaccacgg   1260
ttgcattgat taagtgtggg tatttttcat tccgagccaa ggatattcgg gcgttttact   1320
ttgtgcttta tacatttgtt tactttttct gtatgattcc ggccaggatt actgcaatga   1380
tgacgctttg ggacattggc tggggtactc gcggtggaaa cgagaagcct tccgttggca   1440
cccgggtcgc tctgtgggca aagcaatatc tcattgcata tatgtggtgg gccgcggttg   1500
ttggcgctgg agtttacagc atcgtccata actggatgtt cgattggaat tctctttctt   1560
atcgttttgc tttggttggt atttgttctt acattgtttt tattgttatt gtgctggtgg   1620
tttatttcac cggcaaaatt acgacttgga atttcacgaa gcttcagaag gagctaatcg   1680
aggatcgcgt tctgtacgat gcaactacca atgctcagtc tgtgtgattt ttcctgcaag   1740
```

<210> SEQ ID NO 8
<211> LENGTH: 2937
<212> TYPE: DNA
<213> ORGANISM: Pastuerella Multocida

<400> SEQUENCE: 8

```
atttttaag gacagaaaat gaatacatta tcacaagcaa taaaagcata taacagcaat     60
gactatcaat tagcactcaa attatttgaa aagtcggcgg aaatctatgg acggaaaatt    120
gttgaatttc aaattaccaa atgcaaagaa aaactctcag cacatccttc tgttaattca    180
gcacatcttt ctgtaaataa agaagaaaaa gtcaatgttt gcgatagtcc gttagatatt    240
gcaacacaac tgttactttc caacgtaaaa aaattagtac tttctgactc ggaaaaaaac    300
acgttaaaaa ataaatggaa attgctcact gagaagaaat ctgaaaatgc ggaggtaaga    360
gcggtcgccc ttgtaccaaa agattttccc aaagatctgg ttttagcgcc tttacctgat    420
catgttaatg attttacatg gtacaaaaag cgaaagaaaa gacttggcat aaaacctgaa    480
catcaacatg ttggtctttc tattatcgtt acaacattca atcgaccagc aattttatcg    540
attacattag cctgtttagt aaaccaaaaa acacattacc cgtttgaagt tatcgtgaca    600
gatgatggta gtcaggaaga tctatcaccg atcattcgcc aatatgaaaa taaattggat    660
attcgctacg tcagacaaaa agataacggt tttcaagcca gtgccgctcg gaatatggga    720

```
ttacgcttag caaatatga ctttattggc ttactcgact gtgatatggc gccaaatcca    780
ttatgggttc attcttatgt tgcagagcta ttagaagatg atgatttaac aatcattggt    840
ccaagaaaat acatcgatac acaacatatt gacccaaaag acttcttaaa taacgcgagt    900
ttgcttgaat cattaccaga agtgaaaacc aataatagtg ttgccgcaaa aggggaagga    960
acagtttctc tggattggcg cttagaacaa ttcgaaaaaa cagaaaatct ccgcttatcc   1020
gattcgcctt tccgtttttt tgcggcgggt aatgttgctt tcgctaaaaa atggctaaat   1080
aaatccggtt tctttgatga ggaatttaat cactggggtg gagaagatgt ggaatttgga   1140
tatcgcttat tccgttacgg tagtttcttt aaaactattg atggcattat ggcctaccat   1200
caagagccac caggtaaaga aaatgaaacc gatcgtgaag cgggaaaaaa tattacgctc   1260
gatattatga gagaaaaggt cccttatatc tatagaaaac ttttaccaat agaagattcg   1320
catatcaata gagtaccttt agtttcaatt tatatcccag cttataactg tgcaaactat   1380
attcaacgtt gcgtagatag tgcactgaat cagactgttg ttgatctcga ggtttgtatt   1440
tgtaacgatg gttcaacaga taatacctta gaagtgatca ataagcttta tggtaataat   1500
cctagggtac gcatcatgtc taaaccaaat ggcggaatag cctcagcatc aaatgcagcc   1560
gtttctttg ctaaaggtta ttacattggg cagttagatt cagatgatta tcttgagcct   1620
gatgcagttg aactgtgttt aaaagaattt ttaaaagata aaacgctagc ttgtgtttat   1680
accactaata gaaacgtcaa tccggatggt agcttaatcg ctaatggtta caattggcca   1740
gaattttcac gagaaaaact cacaacggct atgattgctc accactttag aatgttcacg   1800
attagagctt ggcatttaac tgatggattc aatgaaaaaa ttgaaaatgc cgtagactat   1860
gacatgttcc tcaaactcag tgaagttgga aaatttaaac atcttaataa aatctgctat   1920
aaccgtgtat tacatggtga taacacatca attaagaaac ttggcattca aaagaaaaac   1980
cattttgttg tagtcaatca gtcattaaat agacaaggca taacttatta taattatgac   2040
gaatttgatg atttagatga aagtagaaag tatattttca ataaaaccgc tgaatatcaa   2100
gaagagattg atatcttaaa agatattaaa atcatccaga ataaagatgc caaaatcgca   2160
gtcagtattt tttatcccaa tacattaaac ggcttagtga aaaaactaaa caatattatt   2220
gaatataata aaaatatatt cgttattgtt ctacatgttg ataagaatca tcttacacca   2280
gatatcaaaa agaaatact agccttctat cataaacatc aagtgaatat tttactaaat   2340
aatgatatct catattacac gagtaataga ttaataaaaa ctgaggcgca tttaagtaat   2400
attaataaat taagtcagtt aaatctaaat tgtgaataca tcattttga taatcatgac   2460
agcctattcg ttaaaaatga cagctatgct tatatgaaaa aatatgatgt cggcatgaat   2520
ttctcagcat taacacatga ttggatcgag aaaatcaatg cgcatccacc atttaaaaag   2580
ctcattaaaa cttattttaa tgacaatgac ttaaaaagta tgaatgtgaa aggggcatca   2640
caaggtatgt ttatgacgta tgcgctagcg catgagcttc tgacgattat taagaagtc   2700
atcacatctt gccagtcaat tgatagtgtg ccagaatata acactgagga tatttggttc   2760
caatttgcac ttttaatctt agaaaagaaa accggccatg tatttaataa acatcgacc   2820
ctgacttata tgccttggga acgaaaatta caatggacaa atgaacaaat tgaaagtgca   2880
aaaagaggag aaaatatacc tgttaacaag ttcattatta atagtataac tctataa    2937
```

<210> SEQ ID NO 9
<211> LENGTH: 972
<212> TYPE: PRT

<213> ORGANISM: Pastuerella Multocida

<400> SEQUENCE: 9

```
Met Asn Thr Leu Ser G

```
Glu Asn Glu Thr Asp Arg Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
            435                 440                 445

Tyr Asn Cys Ala Asn Tyr Ile Gln Arg Cys Val Asp Ser Ala Leu Asn
450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
                500                 505                 510

Ala Ala Val Ser Phe Ala Lys Gly Tyr Tyr Ile Gly Gln Leu Asp Ser
                515                 520                 525

Asp Asp Tyr Leu Glu Pro Asp Ala Val Glu Leu Cys Leu Lys Glu Phe
            530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
            595                 600                 605

Glu Asn Ala Val Asp Tyr Asp Met Phe Leu Lys Leu Ser Glu Val Gly
    610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
                660                 665                 670

Tyr Asp Glu Phe Asp Asp Leu Asp Glu Ser Arg Lys Tyr Ile Phe Asn
            675                 680                 685

Lys Thr Ala Glu Tyr Gln Glu Glu Ile Asp Ile Leu Lys Asp Ile Lys
            690                 695                 700

Ile Ile Gln Asn Lys Asp Ala Lys Ile Ala Val Ser Ile Phe Tyr Pro
705                 710                 715                 720

Asn Thr Leu Asn Gly Leu Val Lys Lys Leu Asn Asn Ile Ile Glu Tyr
                725                 730                 735

Asn Lys Asn Ile Phe Val Ile Val Leu His Val Asp Lys Asn His Leu
                740                 745                 750

Thr Pro Asp Ile Lys Lys Glu Ile Leu Ala Phe Tyr His Lys His Gln
            755                 760                 765

Val Asn Ile Leu Leu Asn Asn Asp Ile Ser Tyr Tyr Thr Ser Asn Arg
            770                 775                 780

Leu Ile Lys Thr Glu Ala His Leu Ser Asn Ile Asn Lys Leu Ser Gln
785                 790                 795                 800

Leu Asn Leu Asn Cys Glu Tyr Ile Ile Phe Asp Asn His Asp Ser Leu
                805                 810                 815

Phe Val Lys Asn Asp Ser Tyr Ala Tyr Met Lys Lys Tyr Asp Val Gly
```

```
                  820                 825                830
Met Asn Phe Ser Ala Leu Thr His Asp Trp Ile Glu Lys Ile Asn Ala
            835                 840                 845

His Pro Pro Phe Lys Lys Leu Ile Lys Thr Tyr Phe Asn Asp Asn Asp
    850                 855                 860

Leu Lys Ser Met Asn Val Lys Gly Ala Ser Gln Gly Met Phe Met Thr
865                 870                 875                 880

Tyr Ala Leu Ala His Glu Leu Leu Thr Ile Ile Lys Glu Val Ile Thr
                885                 890                 895

Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
            915                 920                 925

Phe Asn Lys Thr Ser Thr Leu Thr Tyr Met Pro Trp Glu Arg Lys Leu
930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970

<210> SEQ ID NO 10
<211> LENGTH: 568
<212> TYPE: PRT
<213> ORGANISM: Paramecium bursaria chorella virus

<400> SEQUENCE: 10

Met Gly Lys Asn Ile Ile Met Val Ser Trp Tyr Thr Ile Ile Thr
1               5                   10                  15

Ser Asn Leu Ile Ala Val Gly Gly Ala Ser Leu Ile Leu Ala Pro Ala
            20                  25                  30

Ile Thr Gly Tyr Val Leu His Trp Asn Ile Ala Leu Ser Thr Ile Trp
        35                  40                  45

Gly Val Ser Ala Tyr Gly Ile Phe Val Phe Gly Phe Phe Leu Ala Gln
    50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Glu Asp Asp Met Arg Met Ala Ala Val Tyr Lys Ala Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Val Leu Ile Asp
        195                 200                 205

Ser Asp Thr Val Leu Glu Lys Asp Ala Ile Leu Glu Val Val Tyr Pro
    210                 215                 220
```

-continued

```
Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Ile Asp Ile Ile Lys
        275                 280                 285

Glu Ile Lys Asp Pro Trp Ile Ser Gln Arg Phe Leu Gly Gln Lys Cys
    290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
        355                 360                 365

Leu Ser Gly Ile Trp Leu Ala Phe Glu Cys Leu Tyr Gln Ile Thr Tyr
    370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Val Ala Leu
                405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Phe Cys Met Ile Pro Ala
            435                 440                 445

Arg Ile Thr Ala Met Met Thr Leu Trp Asp Ile Gly Trp Gly Thr Arg
450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Ala Val Val Gly Ala
            485                 490                 495

Gly Val Tyr Ser Ile Val His Asn Trp Met Phe Asp Trp Asn Ser Leu
            500                 505                 510

Ser Tyr Arg Phe Ala Leu Val Gly Ile Cys Ser Tyr Ile Val Phe Ile
        515                 520                 525

Val Ile Val Leu Val Tyr Phe Thr Gly Lys Ile Thr Thr Trp Asn
    530                 535                 540

Phe Thr Lys Leu Gln Lys Glu Leu Ile Glu Asp Arg Val Leu Tyr Asp
545                 550                 555                 560

Ala Thr Thr Asn Ala Gln Ser Val
                565
```

METHODS OF PRODUCING HYALURONIC ACID USING A RECOMBINANT HYALURONAN SYNTHASE GENE

CROSS-REFERENCE TO RELATED APPLICATIONS

This application is a continuation of U.S. Ser. No. 10/011,768, filed Dec. 11, 2001; which is a continuation of U.S. Ser. No. 09/469,200, filed Dec. 21, 1999, now U.S. Pat. No. 6,833,264, issued Dec. 21, 2004; which is a continuation of U.S. Ser. No. 09/178,851, filed Oct. 26, 1998, now abandoned; and claims priority under 35 U.S.C. § 119(e) of provisional U.S. Ser. No. 60/064,435, filed Oct. 31, 1997; the contents of each of which are hereby expressly incorporated herein in their entirety by reference. Said application U.S. Ser. No. 10/011,768 is also a continuation-in-part of U.S. Ser. No. 09/146,893, filed Sep. 3, 1998, now U.S. Pat. No. 6,455,304, issued Sep. 24, 2002; which is a continuation of U.S. Ser. No. 08/270,581, filed Jul. 1, 1994, now abandoned; the contents of each of which are hereby expressly incorporated herein in their entirety by reference.

STATEMENT REGARDING FEDERALLY SPONSORED RESEARCH OR DEVELOPMENT

The government owns certain rights in the present invention pursuant to grant number GM35978 from the National Institutes of Health.

BACKGROUND OF THE INVENTION

1. Field of the Invention

The present invention relates to a nucleic acid segment having a coding region segment encoding enzymatically active *Streptococcus equisimilis* hyaluronate synthase (seHAS), and to the use of this nucleic acid segment in the preparation of recombinant cells which produce hyaluronate synthase and its hyaluronic acid product. Hyaluronate is also known as hyaluronic acid or hyaluronan.

2. Brief Description of the Related Art

The incidence of streptococcal infections is a major health and economic problem worldwide, particularly in developing countries. One reason for this is due to the ability of Streptococcal bacteria to grow undetected by the body's phagocytic cells, i.e., macrophages and polymorphonuclear cells (PMNs). These cells are responsible for recognizing and engulfing foreign microorganisms. One effective way the bacteria evade surveillance is by coating themselves with polysaccharide capsules, such as a hyaluronic acid (HA) capsule. The structure of HA is identical in both prokaryotes and eukaryotes.

Since HA is generally nonimmunogenic, the encapsulated bacteria do not elicit an immune response and are, therefore, not targeted for destruction. Moreover, the capsule exerts an antiphagocytic effect on PMNs in vitro and prevents attachment of *Streptococcus* to macrophages. Precisely because of this, in Group A and Group C *Streptococci*, the HA capsules are major virulence factors in natural and experimental infections. Group A *Streptococcus* are responsible for numerous human diseases including pharyngitis, impetigo, deep tissue infections, rheumatic fever and a toxic shock-like syndrome. The Group C *Streptococcus equisimilis* is responsible for osteomyelitis, pharyngitis, brain abscesses, and pneumonia.

Structurally, HA is a high molecular weight linear polysaccharide of repeating disaccharide units consisting of N-acetylglucosamine (GlcNAc) and glucuronic acid (GlcA). The number of repeating disaccharides in an HA molecule can exceed 30,000, a $M_r > 10^7$. HA is the only glycosaminoglycan synthesized by both mammalian and bacterial cells particularly Groups A and C *Stereptococci* and Type A *Pasturella multocida*. These strains make HA which is secreted into the medium as well as HA capsules. The mechanism by which these bacteria synthesize HA is of broad interest medicinally since the production of the HA capsule is a very efficient and clever way that *Stereptococci* use to evade surveillance by the immune system.

HA is synthesized by mammalian and bacterial cells by the enzyme hyaluronate synthase which has been localized to the plasma membrane. It is believed that the synthesis of HA in these organisms is a multi-step process. Initiation involves binding of an initial precursor, UDP-GlcNAc or UDP-GlcA. This is followed by elongation which involves alternate addition of the two sugars to the growing oligosaccharide chain. The growing polymer is extruded across the plasma membrane region of the cell and into the extracellular space. Although the HA biosynthetic system was one of the first membrane heteropolysaccharide synthetic pathways studied, the mechanism of HA synthesis is still not well understood. This may be because in vitro systems developed to date are inadequate in that de novo biosynthesis of HA has not been accomplished.

The direction of HA polymer growth is still a matter of disagreement among those of ordinary skill in the art. Addition of the monosaccharides could be to the reducing or nonreducing end of the growing HA chain. Furthermore, questions remain concerning (i) whether nascent chains are linked covalently to a protein, to UDP or to a lipid intermediate, (ii) whether chains are initiated using a primer, and (iii) the mechanism by which the mature polymer is extruded through the plasma membrane of the *Streptococcus*. Understanding the mechanism of HA biosynthesis may allow development of alternative strategies to control Streptococcal and Pasturella infections by interfering in the process.

HA has been identified in virtually every tissue in vertebrates and has achieved widespread use in various clinical applications, most notably and appropriately as an intra-articular matrix supplement and in eye surgery. The scientific literature has also shown a transition from the original perception that HA is primarily a passive structural component in the matrix of a few connective tissues and in the capsule of certain strains of bacteria to a recognition that this ubiquitous macromolecule is dynamically involved in many biological processes: from modulating cell migration and differentiation during embryogenesis to regulation of extracellular matrix organization and metabolism to important roles in the complex processes of metastasis, wound healing, and inflammation. Further, it is becoming clear that HA is highly metabolically active and that cells focus much attention on the processes of its synthesis and catabolism. For example, the half-life of HA in tissues ranges from 1 to 3 weeks in cartilage to <1 day in epidermis.

It is now clear that a single protein utilizes both sugar substrates to synthesize HA. The abbreviation HAS, for the HA synthase, has gained widespread support for designating this class of enzymes. Markovitz et al. successfully characterized the HAS activity from *Streptococcus pyogenes* and discovered the enzymes's membrane localization and its requirements for sugar nucleotide precursors and $Mg^{2+}$. Prehm found that elongating HA, made by B6 cells, was digested by hyaluronidase added to the medium and proposed that HAS resides at the plasma membrane. Philipson and Schwartz also showed that HAS activity cofractionated with plasma membrane markers in mouse oligodendroglioma cells.

HAS assembles high $M_r$ HA that is simultaneously extruded through the membrane into the extracellular space (or to make the cell capsule in the case of bacteria) as glycosaminoglycan synthesis proceeds. This mode of biosynthesis is unique among macromolecules since nucleic acids, proteins, and lipids are synthesized in the nucleus, endoplasmic reticulum/Golgi, cytoplasm, or mitochondria. The extrusion of the growing chain into the extracellular space also allows for unconstrained polymer growth, thereby achieving the exceptionally large size of HA, whereas confinement of synthesis within a Golgi or post-Golgi compartment could limit the overall amount or length of the polymers formed. High concentrations of HA within a confined lumen could also create a high viscosity environment that might be deleterious for other organelle functions.

Several studies attempted to solubilize, identify, and purify HAS from strains of Streptococci that make a capsular coat of HA as well as from eukaryotic cells. Although the streptococcal and murine oligodendroglioma enzymes were successfully detergent-solubilized and studied, efforts to purify an active HAS for further study or molecular cloning remained unsuccessful for decades. Prehm and Mausolf used periodate-oxidized UDP-GlcA or UDP-GlcNAc to affinity label a protein of ~52 kDa in streptococcal membranes that co-purified with HAS. This led to a report claiming that the Group C streptococcal HAS had been cloned, which was unfortunately erroneous. This study failed to demonstrate expression of an active synthase and may have actually cloned a peptide transporter. Triscott and van de Rijn used digitonin to solubilize HAS from streptococcal membranes in an active form. Van de Rijn and Drake selectively radiolabeled three streptococcal membrane proteins of 42, 33, and 27 kDa with 5-azido-UDP-GlcA and suggested that the 33-kDa protein was HAS. As shown later, however, HAS actually turned out to be the 42-kDa protein.

Despite these efforts, progress in understanding the regulation and mechanisms of HA synthesis was essentially stalled, since there were no molecular probes for HAS mRNA or HAS protein. A major breakthrough occurred in 1993 when DeAngelis et al. reported the molecular cloning and characterization of the Group A streptococcal gene encoding the protein HasA. This gene was known to be in part of an operon required for bacterial HA synthesis, although the function of this protein, which is now designated as spHAS (the S. pyogenes HAS), was unknown. spHAS was subsequently proven to be responsible for HA elongation and was the first glycosaminoglycan synthase identified and cloned and then successfully expressed. The S. pyogenes HA synthesis operon encodes two other proteins. HasB is a UDP-glucose dehydrogenase, which is required to convert UDP-glucose to UDP-GlcA, one of the substrates for HA synthesis. HasC is a UDP-glucose pyrophosphorylase, which is required to convert glucose 1-phosphate and UTP to UDP-glucose. Co-transfection of both hasA and hasB genes into either acapsular Streptococcus strains or Enteroccus faecalis conferred them with the ability to synthesize HA and form a capsule. This provided the first strong evidence that HasA is an HA synthase.

The elusive HA synthase gene was finally cloned by a transposon mutagenesis approach, in which an acapsular mutant Group A strain was created containing a transposon interruption of the HA synthesis operon. Known sequences of the transposon allowed the region of the junction with streptococcal DNA to be identified and then cloned from wild-type cells. The encoded spHAS was 5–10% identical to a family of yeast chitin synthases and 30% identical to the Xenopuslaevis protein DG42 developmentally expressed during gastrulation), whose function was unknown at the time. DeAngelis and Weigel expressed the active recombinant spHAS in Escherichia coli and showed that this single purified gene product synthesizes high $M_r$ HA when incubated in vitro with UDP-GlcA and UDP-GlcNAc, thereby showing that both glycosyltransferase activities required for HA synthesis are catalyzed by the same protein, as first proposed in 1959. This set the stage for the almost simultaneous identification of eukaryotic HAS cDNAs in 1996 by four laboratories revealing that HAS is a multigene family encoding distinct isozymes. Two genes (HAS1 and HAS2) were quickly discovered in mammals (29–34), and a third gene HAS3 was later discovered. A second streptococcal seHAS or Streptococcus equisimilis hyaluronate synthase, has now been found and is the invention being claimed and disclosed herein.

As indicated, we have also identified the authentic HAS gene from Group C Streptococcus equisimilis (seHAS); the seHAS protein has a high level of identity (approximately 70 percent) to the spHAS enzyme. This identity, however, is interesting because the seHAS gene does not cross-hybridize to the spHAS gene.

Membranes prepared from E. coli expressing recombinant seHAS synthesize HA when both substrates are provided. The results confirm that the earlier report of Lansing et al. claiming to have cloned the Group C HAS was wrong. Unfortunately, several studies have employed antibody to this uncharacterized 52-kDa streptococcal protein to investigate what was believed to be eukaryotic HAS.

Itano and Kimata used expression cloning in a mutant mouse mammary carcinoma cell line, unable to synthesize HA, to clone the first putative mammalian HAS cDNA (mmHAS1). Subclones defective in HA synthesis fell into three separate classes that were complementary for HA synthesis in somatic cell fusion experiments, suggesting that at least three proteins are required. Two of these classes maintained some HA synthetic activity, whereas one showed none. The latter cell line was used in transient transfection experiments with cDNA prepared from the parental cells to identify a single protein that restored HA synthetic activity. Sequence analyses revealed a deduced primary structure for a protein of ~65 kDa with a predicted membrane topology similar to that of spHAS. mmHAS1 is 30% identical to spHAS and 55% identical to DG42. The same month this report appeared, three other groups submitted papers describing cDNAs encoding what was initially thought to be the same mouse and human enzyme. However, through an extraordinary circumstance, each of the four laboratories had discovered a separate HAS isozyme in both species.

Using a similar functional cloning approach to that of Itano and Kimata, Shyjan et al. identified the human homolog of HAS 1. A mesenteric lymph node cDNA library was used to transfect murine mucosal T lymphocytes that were then screened for their ability to adhere in a rosette assay. Adhesion of one transfectant was inhibited by antisera to CD44, a known cell surface HA-binding protein, and was abrogated directly by pretreatment with hyaluronidase. Thus, rosetting by this transfectant required synthesis of HA. Cloning and sequencing of the responsible cDNA identified hsHAS1. Itano and Kimata also reported a human HAS1 cDNA isolated from a fetal brain library. The hsHAS1 cDNAs reported by the two groups, however, differ in length; they encode a 578 or a 543 amino acid protein. HAS activity has only been demonstrated for the longer form.

Based on the molecular identification of spHAS as an authentic HA synthase and regions of near identity among DG42, spHAS, and NodC (a β-GlcNAc transferase nodulation factor in *Rhizobium*), Spicer et al. used a degenerate RT-PCR approach to clone a mouse embryo cDNA encoding a second distinct enzyme, which is designated mmHAS2. Transfection of mmHAS2 cDNA into COS cells directed de novo production of an HA cell coat detected by a particle exclusion assay, thereby providing strong evidence that the HAS2 protein can synthesize HA. Using a similar approach, Watanabe and Yamaguchi screened a human fetal brain cDNA library to identify hsHAS2. Fulop et al. independently used a similar strategy to identify mmHAS2 in RNA isolated from ovarian cumulus cells actively synthesizing HA, a critical process for normal cumulus oophorus expansion in the pre-ovulatory follicle. Cumulus cell-oocyte complexes were isolated from mice immediately after initiating an ovulatory cycle, before HA synthesis begins, and at later times when HA synthesis is just beginning (3 h) or already apparent (4 h). RT-PCR showed that HAS2 mRNA was absent initially but expressed at high levels 3–4 h later suggesting that transcription of HAS2 regulates HA synthesis in this process. Both hsHAS2 are 552 amino acids in length and are 98% identical. mmHAS1 is 583 amino acids long an 95% identical to hsHAS1, which is 578 amino acids long.

Most recently Spicer et al. used a PCR approach to identify a third HAS gene in mammals. The mmHAS3 protein is 554 amino acids long and 71, 56, and 28% identical, respectively, to mmHAS1, mmHAS2, DG42, and spHAS. Spicer et al. have also localized the three human and mouse genes to three different chromosomes (HAS1 to hsChr 19/mmChr 17; HAS2 to hsChr 8/mmChr 15; HAS3 to hsChr 16/mmChr 8). Localization of the three HAS genes on different chromosomes and the appearance of HA throughout the vertebrate class suggest that this gene family is ancient and that isozymes appeared by duplication early in the evolution of vertebrates. The high identity (~30%) between the bacterial and eukaryotic HASs also suggests that the two had a common ancestral gene. Perhaps primitive bacteria usurped the HAS gene from an early vertebrate ancestor before the eukaryotic gene products became larger and more complex. Alternatively, the bacteria could have obtained a larger vertebrate HAS gene and deleted regulatory sequences nonessential for enzyme activity.

The discovery of *X. laevis* DG42 by Dawid and coworkers played a significant role in these recent developments, even though this protein was not known to be an HA synthase. Nonetheless, that DG42 and spHAS were 30% identical was critical for designing oligonucleotides that allowed identification of mammalian HAS2. Ironically, definitive evidence that DG42 is a bona fide HA synthase was reported only after the discoveries of the Mammalian isozymes, when DeAngelis and Achyuthan expressed the recombinant protein in yeast (an organism that cannot synthesize HA) and showed that it synthesizes HA when isolated membranes are provided with the two substrates. Meyer and Kreil also showed that lysates from cells transfected with cDNA for DG42 synthesize elevated levels of HA. Now that its function is known, DG42 can, therefore, be designated XIHAS.

There are common predicted structural features shared by all the HAS proteins, including a large central domain and clusters of 2–3 transmembrane or membrane-associated domains at both the amino and carboxyl ends of the protein. The central domain, which comprises up to ~88% of the predicted intracellular HAS protein sequences, probably contains the catalytic regions of the enzyme. This predicted central domain is 264 amino acids long in spHAS (63% of the total protein) and 307–328 residues long in the eukaryotic HAS members (54–56% of the total protein). The exact number and orientation of membrane domains and the topological organization of extracellular and intracellular loops have not yet been experimentally determined for any HAS.

spHAS is a HAS family member that has been purified and partially characterized. Initial studies using spHAS/alkaline phosphatase fusion proteins indicate that the N terminus, C terminus, and the large central domain of spHAS are, in fact, inside the cell. spHAS has 6 cysteines, whereas HAS1, HAS2, and HAS3 have 13, 14 and 14 Cys residues, respectively. Two of the 6 Cys residues in spHAS are conserved and identical in HAS1 and HAS2. Only one conserved Cys residue is found at the same position (Cys-225 in spHAS) in all the HAS family members. This may be an essential Cys whose modification by sulfhydryl poisons partially inhibits enzyme activity. The possible presence of disulfide bonds or the identification of critical Cys residues needed for any of the multiple HAS functions noted below has not yet been elucidated for any members of the HAS family.

In addition to the proposed unique mode of synthesis at the plasma membrane, the HAS enzyme family is highly unusual in the large number of functions required for the overall polymerization of HA. At least six discrete activities are present within the HAS enzyme: binding sites for each of the two different sugar nucleotide precursors (UDP-GlcNAc and UDP-GlcA), two different glycosyltransferase activities, one or more binding sites that anchor the growing HA polymer to the enzyme (perhaps related to a B—$X_7$—B motif), and a ratchet-like transfer reaction that moves the growing polymer one sugar at a time. This later activity is likely coincident with the stepwise advance of the polymer through the membrane. All of these functions, and perhaps others as yet unknown, are present in a relatively small protein ranging in size from 419 (spHAS) to 588 (XHAS) amino acids.

Although all the available evidence supports the conclusion that only the spHAS protein is required for HA biosynthesis in bacteria or in vitro, it is possible that the larger eukaryotic HAS family members are part of multicomponent complexes. Since the eukaryotic HAS proteins are ~40% larger than spHAS, their additional protein domains could be involved in more elaborate functions such as intracellular trafficking and localization, regulation of enzyme activity, and mediating interactions with other cellular components.

The unexpected finding that there are multiple vertebrate HAS genes encoding different synthases strongly supports the emerging consensus that HA is an important regulator of cell behavior and not simply a structural component in tissues. Thus, in less than six months, the field moved from one known, cloned HAS (spHAS) to recognition of a multigene family that promises rapid, numerous, and exciting future advances in our understanding of the synthesis and biology of HA.

For example, disclosed hereinafter are the sequences of the two HAS genes: from *Pasturella multocida*; and (2) *Paramecium bursaria* chlorella virus (PBCV-1). The presence of hyaluronan synthase in these two systems and the purification and use of the hyaluronan synthase from these two different systems indicates an ability to purify and isolate nucleic acid sequences encoding enzymatically active hyaluronan synthase in many different prokaryotic and viral sources.

Group C *Streptococcus equisimilis* strain D181 synthesizes and secretes hyaluronic acid (HA). Investigators have used this strain and Group A *Streptococcus pyogene* strains, such as S43 and A111, to study the biosynthesis of HA and to characterize the HA-synthesizing activity in terms of its divalent cation requirement, precursor (UDP-GlcNAc and UDP-GlcA) utilization, and optimum pH.

Traditionally, HA has been prepared commercially by isolation from either rooster combs or extracellular media from Streptococcal cultures. One method which has been developed for preparing HA is through the use of cultures of HA-producing Streptococcal bacteria. U.S. Pat. No. 4,517,295 describes such a procedure wherein HA-producing Stereptococci are fermented under anaerobic conditions in a $CO_2$-enriched growth medium. Under these conditions, HA is produced and can be extracted from the broth. It is generally felt that isolation of HA from rooster combs is laborious and difficult, since one starts with HA in a less pure state. The advantage of isolation from rooster combs is that the HA produced is of higher molecular weight. However, preparation of HA by bacterial fermentation is easier, since the HA is of higher purity to start with. Usually, however, the molecular weight of HA produced in this way is smaller than that from rooster combs. Therefore, a technique that would allow the production of high molecular weight HA by bacterial fermentation would be an improvement over existing procedures.

High molecular weight HA has a wide variety of useful applications—ranging from cosmetics to eye surgery. Due to its potential for high viscosity and its high biocompatibility, HA finds particular application in eye surgery as a replacement for vitreous fluid. HA has also been used to treat racehorses for traumatic arthritis by intra-articular injections of HA, in shaving cream as a lubricant, and in a variety of cosmetic products due to its physiochemical properties of high viscosity and its ability to retain moisture for long periods of time. In fact, in August of 1997 the U.S. Food and Drug Agency approved the use of high molecular weight HA in the treatment of severe arthritis through the injection of such high molecular weight HA directly into the affected joints. In general, the higher molecular weight HA that is employed the better. This is because HA solution viscosity increases with the average molecular weight of the individual HA polymer molecules in the solution. Unfortunately, very high molecular weight HA, such as that ranging up to $10^7$, has been difficult to obtain by currently available isolation procedures.

To address these or other difficulties, there is a need for new methods and constructs that can be used to produce HA having one or more improved properties such as greater purity or ease of preparation. In particular, there is a need to develop methodology for the production of larger amounts of relatively high molecular weight and relatively pure HA than is currently commercially available. There is yet another need to be able to develop methodology for the production of HA having a modified size distribution ($H_{Asize}$) as well as HA having a modified structure ($H_{Amod}$).

The present invention addresses one or more shortcomings in the art. Using recombinant DNA technology, a purified nucleic acid segment having a coding region encoding enzymatically active seHAS is disclosed and claimed in conjunction, with methods to produce an enzymatically active HA synthase, as well as methods for using the nucleic acid segment in the preparation of recombinant cells which produce HAS and its hyaluronic acid product.

Thus, it is an object of the present invention to provide a purified nucleic acid segment having a coding region encoding enzymatically active HAS.

It is a further object of the present invention to provide a recombinant vector which includes a purified nucleic acid segment having a coding region encoding enzymatically active HAS.

It is still a further object of the present invention to provide a recombinant host cell transformed with a recombinant vector which includes a purified nucleic acid segment having a coding region encoding enzymatically active HAS.

It is yet another object of the present invention to provide a method for detecting a bacterial cell that expresses HAS.

It is another object of the present invention to provide a method for producing high and/or low molecular weight hyaluronic acid from a hyaluronate synthase gene, such as seHAS, as well as methods for producing HA having a modified size distribution and/or a modified structure.

These and other objects of the present invention will become apparent in light of the attached specification, claims, and drawings.

BRIEF SUMMARY OF THE INVENTION

The present invention involves the application of recombinant DNA technology to solving one or more problems in the art of hyaluronic acid (HA) preparation. These problems are addressed through the isolation and use of a nucleic acid segment having a coding region encoding the enzymatically active *Streptococcus equisimilis* (seHAS) hyaluronate synthase gene, a gene responsible for HA chain biosynthesis. The seHAS gene was cloned from DNA of an appropriate microbial source and engineered into useful recombinant constructs for the preparation of HA and for the preparation of large quantities of the HAS enzyme itself.

The present invention encompasses a novel gene, seHAS. The expression of this gene correlates with virulence of streptococcal Group A and Group C strains, by providing a means of escaping phagocytosis and immune surveillance. The terms "hyaluronic acid synthase", "hyaluronate synthase", "hyaluronan synthase", and "HA synthase" are used interchangeably to describe an enzyme that polymerizes a glycosaminoglycan polysaccharide chain composed of alternating glucuronic acid and N-acetylglucosamine sugars, β 1,3 and β 1,4 linked. The term "seHAS" describes the HAS enzyme derived from *Streptococcus equisimilis*.

The present invention concerns the isolation and characterization of a hyaluronate or hyaluronic acid synthase gene, cDNA, and gene product (HAS), as may be used for the polymerization of glucuronic acid and N-acetylglucosamine into the glycosaminoglycan hyaluronic acid. The present invention identifies the seHAS locus and discloses the nucleic acid sequence which encodes for the enzymatically active seHAS gene from *Streptococcus equisimilis*. The HAS gene also provides a new probe to assess the potential of bacterial specimens to produce hyaluronic acid.

Through the application of techniques and knowledge set forth herein, those of skill in the art will be able to obtain nucleic acid segments encoding the seHAS gene. As those of skill in the art will recognize, in light of the present disclosure, these advantages provide significant utility in being able to control the expression of the seHAS gene and control the nature of the seHAS gene product, the seHAS enzyme, that is produced.

Accordingly, the invention is directed to the isolation of a purified nucleic acid segment which has a coding region encoding enzymatically active HAS, whether it be from prokaryotic or eukaryotic sources. This is possible because the enzyme, and indeed the gene, is one found in both eukaryotes and some prokaryotes. Eukaryotes are also known to produce HA and thus have HA synthase genes that can be employed in connection with the invention.

HA synthase-encoding nucleic acid segments of the present invention are defined as being isolated free of total chromosomal or genomic DNA such that they may be readily manipulated by recombinant DNA techniques. Accordingly, as used herein, the phrase "a purified nucleic acid segment" refers to a DNA segment isolated free of unrelated chromosomal or genomic DNA and retained in a state rendering it useful for the practice of recombinant techniques, such as DNA in the form of a discrete isolated DNA fragment, or a vector (e.g., plasmid, phage or virus) incorporating such a fragment.

A preferred embodiment of the present invention is a purified nucleic acid segment having a coding region encoding enzymatically active HAS. In particular, the purified nucleic acid segment encodes the seHAS of SEQ ID NO:2 or the purified nucleic acid segment comprises a nucleotide sequence in accordance with SEQ ID NO:1.

Another embodiment of the present invention comprises a purified nucleic acid segment having a coding region encoding enzymatically active HAS and the purified nucleic acid segment is capable of hybridizing to the nucleotide sequence of SEQ ID NO:1.

The present invention also comprises a natural or recombinant vector consisting of a plasmid, cosmid, phage, or virus vector. The recombinant vector may also comprise a purified nucleic acid segment having a coding region encoding enzymatically active HAS.

In particular, the purified nucleic acid segment encodes the seHAS of SEQ ID NO:2 or the purified nucleic acid segment comprises a nucleotide sequence in accordance with SEQ ID NO:1. If the recombinant vector is a plasmid, it may further comprise an expression vector. The expression vector may also include a promoter operatively linked to the enzymatically active HAS coding region.

In another preferred embodiment, the present invention comprises a recombinant host cell such as a prokaryotic cell transformed with a recombinant vector. The recombinant vector includes a purified nucleic acid segment having a coding region encoding enzymatically active HAS. In particular, the purified nucleic acid segment encodes the seHAS of SEQ ID NO:2 or the purified nucleic acid segment comprises a nucleotide sequence in accordance with SEQ ID NO:1.

The present invention also comprises a recombinant host cell, such as an eukaryotic cell transfected with a recombinant vector comprising a purified nucleic acid segment having a coding region encoding enzymatically active HAS. In particular, the purified nucleic acid segment encodes the seHAS of SEQ ID NO:2 or the purified nucleic acid segment comprises a nucleotide sequence in accordance with SEQ ID NO:1. The concept is to create a specifically modified seHAS gene that encodes an enzymatically active HAS capable of producing a hyaluronic acid polymer having a modified structure or a modified size distribution.

The present invention further comprises a recombinant host cell which is electroporated to introduce a recombinant vector into the recombinant host cell. The recombinant vector may include a purified nucleic acid segment having a coding region encoding enzymatically active HAS. In particular, the purified nucleic acid segment encodes the seHAS of SEQ ID NO:2 or the purified nucleic acid segment comprises a nucleotide sequence in accordance with SEQ ID NO:1. The enzymatically active HAS may also be capable of producing a hyaluronic acid polymer having a modified structure or a modified size distribution.

In yet another preferred embodiment, the present invention comprises a recombinant host cell which is transduced with a recombinant vector which includes a purified nucleic acid segment having a coding region encoding enzymatically active HAS. In particular, the purified nucleic acid segment encodes the seHAS of SEQ ID NO:2 or the purified nucleic acid segment comprises a nucleotide sequence in accordance with SEQ ID NO:1. The enzymatically active HAS is also capable of producing a hyaluronic acid polymer having a modified structure or a modified size distribution.

The present invention also comprises a purified composition, wherein the purified composition comprises a polypeptide having a coding region encoding enzymatically active HAS and further having an amino acid sequence in accordance with SEQ ID NO:2.

In another embodiment, the invention comprises a method for detecting a DNA species, comprising the steps of: (1) obtaining a DNA sample; (2) contacting the DNA sample with a purified nucleic acid segment in accordance with SEQ ID NO:1; (3) hybridizing the DNA sample and the purified nucleic acid segment thereby forming a hybridized complex; and (4) detecting the complex.

The present invention also comprises a method for detecting a bacterial cell that expresses mRNA encoding seHAS, comprising the steps of: (1) obtaining a bacterial cell sample; (2) contacting at least one nucleic acid from the bacterial cell sample with purified nucleic acid segment in accordance with SEQ ID NO:1; (3) hybridizing the at least one nucleic acid and the purified nucleic acid segment thereby forming a hybridized complex; and (4) detecting the hybridized complex, wherein the presence of the hybridized complex is indicative of a bacterial strain that expresses mRNA encoding seHAS.

The present invention also comprises methods for detecting the presence of either seHAS or spHAS in a cell. In particular, the method comprises using the oligonucleotides set forth in Seq. ID Nos.: 3–8 as probes. These oligonucleotides would a allow a practitioner to search and detect the presence of seHAS or spHAS in a cell.

The present invention further comprises a method for producing hyaluronic acid, comprising the steps of: (1) introducing a purified nucleic acid segment having a coding region encoding enzymatically active HAS into a host organism, wherein the host organism contains nucleic acid segments encoding enzymes which produce UDP-GlcNAc and UDP-GlcA; (2) growing the host organism in a medium to secrete hyaluronic acid; and (3) recovering the secreted hyaluronic acid.

The method may also include the step of extracting the secreted hyaluronic acid from the medium as well as the step of purifying the extracted hyaluronic acid. Furthermore, the host organism may secrete a structurally modified hyaluronic acid or a size modified hyaluronic acid.

The present invention further comprises a pharmaceutical composition comprising a preselected pharmaceutical drug and an effective amount of hyaluronic acid produced by a recombinant HAS. The pharmaceutical composition may have a hyaluronic acid having a modified molecular weight pharmaceutical composition capable of evading an immune response. The modified molecular weight may also produce a pharmaceutical composition capable of targeting a specific tissue or cell type within the patient having an affinity for the modified molecular weight pharmaceutical composition.

The present invention also comprises a purified and isolated nucleic acid sequence encoding enzymatically active seHAS, where the nucleic acid sequence is (a) the nucleic acid sequence in accordance with SEQ ID NO:1; (b) complementary nucleic acid sequences to the nucleic acid sequence in accordance with SEQ ID NO:1; (c) nucleic acid sequences which will hybridize to the nucleic acid in accordance with SEQ ID NO:1; and (d) nucleic acid sequences which will hybridize to the complementary nucleic acid sequences of SEQ ID NO:1.

The present invention further comprises a purified and isolated nucleic acid segment consisting essentially of a nucleic acid segment encoding enzymatically active HAS.

The present invention also comprises an isolated nucleic acid segment consisting essentially of a nucleic acid segment encoding seHAS having a nucleic acid segment sufficiently duplicative of the nucleic acid segment in accordance of SEQ ID NO:1 to allow possession of the biological property of encoding for an enzymatically active HAS. The nucleic acid segment may also be a cDNA sequence.

The present invention also comprises a purified nucleic acid segment having a coding region encoding enzymatically active HAS, wherein the purified nucleic acid segment is capable of hybridizing to the nucleotide sequence in accordance with SEQ ID NO:1.

BRIEF DESCRIPTION OF THE SEVERAL VIEWS OF THE DRAWINGS

FIG. 2 figuratively depicts the relatedness of seHAS to the bacterial and eukaryotic HAS proteins.

DETAILED DESCRIPTION OF THE INVENTION

Figure 1:
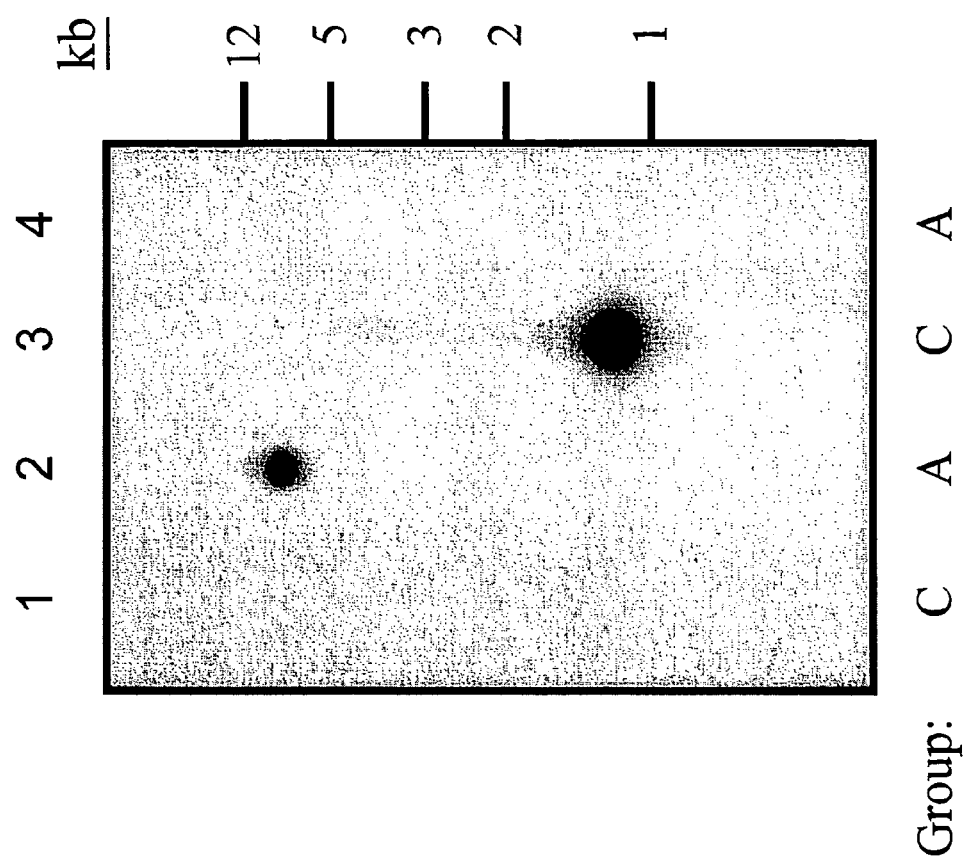
FIG. 1 depicts that cross hybridization between seHAS and spHAS genes does not occur.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Hyaluronate Synthase ("HAS") coding sequence yet is isolated away from, or purified free from, unrelated genomic DNA, for example, total *Streptococcus equisimilis* or, for example, mammalian host genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified seHAS gene refers to a DNA segment including HAS coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest, in this case seHAS, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Due to certain advantages associated with the use of prokaryotic sources, one will likely realize the most advantages upon isolation of the HAS gene from prokaryotes such as *S. pyogenes, S. equisimilis*, or *P. multocida*. One such advantage is that, typically, eukaryotic enzymes may require significant post-translational modifications that can only be achieved in a eukaryotic host. This will tend to limit the applicability of any eukaryotic HA synthase gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library, and (b) the ease of manipulation because the overall size of the coding region of a prokaryotic gene is significantly smaller due to the absence of introns. Furthermore, if the product of the seHAS gene (i.e., the enzyme) requires posttranslational modifications, these would best be achieved in a similar prokaryotic cellular environment (host) from which the gene was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences which encode a seHAS gene, that includes within its amino acid sequence an amino acid sequence in accordance with SEQ ID NO:2. Moreover, in other particular embodiments, the invention concerns isolated DNA segments and recombinant vectors incorporating DNA sequences which encode a gene that includes within its amino acid sequence the amino acid sequence of an HAS gene or DNA, and in particular to an HAS gene or cDNA, corresponding to *Streptococcus equisimilis* HAS. For example, where the DNA segment or vector encodes a full length HAS protein, or is intended for use in expressing the HAS protein, preferred sequences are those which are essentially as set forth in SEQ ID NO:2.

Nucleic acid segments having HA synthase activity may be isolated by the methods described herein. The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein, as a gene having a sequence essentially as set forth in SEQ ID NO:2, and that is associated with the ability of prokaryotes to produce HA or a hyaluronic acid coat.

For instance, the seHAS and spHAS coding sequences are approximately 70% identical and rich in the bases adenine (A) and thymine (T). SeHAS base content is A-26.71%, C-19.13%, G-20.81%, and T-33.33% (A/T=60%). Whereas spHAS is A-31.34%, C-16.42%, G-16.34%, and T-35.8% (A/T=67%). Those of ordinary skill in the art would be surprised that the seHAS coding sequence does not hybridize with the spHAS gene and vice versa, despite their being 70% identical. This unexpected inability to cross-hybridize could be due to short interruptions of mismatched bases throughout the open reading frames. The inability of spHAS and seHAS to cross-hybridize is shown in FIG. 1. The longest stretch of identical nucleotides common to both the seHAS and the spHAS coding sequences is only 20 nucleotides. In addition, the very A–T rich sequences will form less stable hybridization complexes than G-C rich sequences. Another possible explanation could be that there are several stretches of As or Ts in both sequences that could hybridize in a misaligned and unstable manner. This would put the seHAS and spHAS gene sequences out of frame with respect to each other, thereby decreasing the probability of productive hybridization.

Because of this unique phenomena of two genes encoding proteins which are 70% identical not being capable of cross-hybridizing to one another, it is beneficial to think of the claimed nucleic acid segment in terms of its function; i.e., a nucleic acid segment which encodes enzymatically active hyaluronate synthase. One of ordinary skill in the art would appreciate that a nucleic acid segment encoding enzymatically active hyaluronate synthase may contain conserved or semi-conserved substitutions to the sequences set forth in SEQ ID NOS: 1 and 2 and yet still be within the scope of the invention.

In particular, the art is replete with examples of practitioners ability to make structural changes to a nucleic acid segment (i.e., encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1019–1029 (1988) [" . . . according to the observed exchangeability of amino acid side chains, only four groups could be delineated: (i) Ile and Val; (ii) Leu and Met; (iii) Lys, Arg, and Gln, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481–497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216–226 (1992) ["Analysis of the pattern of observed substitutions as a function of local environment shows that there are distinct patterns . . . " Compatible changes can be made.]

These references and countless others, indicate that one of ordinary skill in the art, given a nucleic acid sequence, could make substitutions and changes to the nucleic acid sequence without changing its functionality. Also, a substituted nucleic acid segment may be highly identical and retain its enzymatic activity with regard to its unadulterated parent, and yet still fail to hybridize thereto.

The invention discloses nucleic acid segments encoding enzymatically active hyaluronate synthase—seHAS and spHAS. Although seHAS and spHAS are 70% identical and both encode enzymatically active hyaluronate synthase, they do not cross hybridize. Thus, one of ordinary skill in the art would appreciate that substitutions can be made to the seHAS nucleic acid segment listed in SEQ ID NO: 1 without deviating outside the scope and claims of the present invention. Standardized and accepted functionally equivalent amino acid substitutions are presented in Table I.

TABLE I

| Amino Acid Group | Conservative and Semi-Conservative Substitutions |
| --- | --- |
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Another preferred embodiment of the present invention is a purified nucleic acid segment that encodes a protein in accordance with SEQ ID NO:2, further defined as a recombinant vector. As used herein, the term "recombinant vector" refers to a vector that has been modified to contain a nucleic acid segment that encodes an HAS protein, or fragment thereof. The recombinant vector may be further defined as an expression vector comprising a promoter operatively linked to said HAS encoding nucleic acid segment.

A further preferred embodiment of the present invention is a host cell, made recombinant with a recombinant vector comprising an HAS gene. The preferred recombinant host cell may be a prokaryotic cell. In another embodiment, the recombinant host cell is a eukaryotic cell. As used herein, the term "engineered" or "recombinant" cell is intended to refer to a cell into which a recombinant gene, such as a gene encoding HAS, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene.

Where one desires to use a host other than *Streptococcus*, as may be used to produce recombinant HA synthase, it may be advantageous to employ a prokaryotic system such as *E. coli, B. subtilis, Lactococcus* sp., or even eukaryotic systems such as yeast or Chinese hamster ovary, African green monkey kidney cells, VERO cells, or the like. Of course, where this is undertaken it will generally be desirable to bring the HA synthase gene under the control of sequences which are functional in the selected alternative host. The appropriate DNA control sequences, as well as their construction and use, are generally well known in the art as discussed in more detail hereinbelow.

In preferred embodiments, the HA synthase-encoding DNA segments further include DNA sequences, known in the art functionally as origins of replication or "replicons", which allow replication of contiguous sequences by the particular host. Such origins allow the preparation of extra-chromosomally localized and replicating chimeric segments or plasmids, to which HA synthase DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HA synthase coding gene sequence together with an appropriate replication origin and under the control of selected control regions.

Thus, it will be appreciated by those of skill in the art that other means may be used to obtain the HAS gene or cDNA, in light of the present disclosure. For example, polymerase chain reaction or RT-PCR produced DNA fragments may be obtained which contain full complements of genes or cDNAs from a number of sources, including other strains of *Streptococcus* or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HA synthase.

Once the DNA has been isolated it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both *Lactococcus* or *Bacillus* strains and *E. coli* are employed.

Vectors such as these, exemplified by the pSA3 vector of Dao and Ferretti or the pAT19 vector of Trieu-Cuot, et al., allow one to perform clonal colony selection in an easily manipulated host such as *E. coli*, followed by subsequent transfer back into a food grade *Lactococcus* or *Bacillus* strain for production of HA. These are benign and well studied organisms used in the production of certain foods and biotechnology products. These are advantageous in that one can augment the *Lactococcus* or *Bacillus* strain's ability to synthesize HA through gene dosaging (i.e., providing extra copies of the HA synthase gene by amplification) and/or inclusion of additional genes to increase the availability of HA precursors. The inherent ability of a bacterium to synthesize HA can also be augmented through the formation of extra copies, or amplification, of the plasmid that carries the HA synthase gene. This amplification can account for up to a 10-fold increase in plasmid copy number and, therefore, the HA synthase gene copy number.

Another procedure that would further augment HA synthase gene copy number is the insertion of multiple copies of the gene into the plasmid. Another technique would include integrating the HAS gene into chromosomal DNA. This extra amplification would be especially feasible, since the bacterial HA synthase gene size is small. In some scenarios, the chromosomal DNA-ligated vector is employed to transfect the host that is selected for clonal screening purposes such as *E. coli*, through the use of a vector that is capable of expressing the inserted DNA in the chosen host.

Where a eukaryotic source such as dermal or synovial fibroblasts or rooster comb cells is employed, one will desire to proceed initially by preparing a cDNA library. This is carried out first by isolation of mRNA from the above cells, followed by preparation of double stranded cDNA using an enzyme with reverse transcriptase activity and ligation with the selected vector. Numerous possibilities are available and known in the art for the preparation of the double stranded cDNA, and all such techniques are believed to be applicable. A preferred technique involves reverse transcription. Once a population of double stranded cDNAs is obtained, a cDNA library is prepared in the selected host by accepted techniques, such as by ligation into the appropriate vector and amplification in the appropriate host. Due to the high number of clones that are obtained, and the relative ease of screening large numbers of clones by the techniques set forth herein, one may desire to employ phage expression vectors, such as λgt11, λgt12, λGem11, and/or λZAP for the cloning and expression screening of cDNA clones.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1, and has relatively few codons which are not identical, or functionally equivalent, to the codons of SEQ ID NO:1. The term "functionally equivalent codon" is used herein to refer to codons that encode the same amino acid, such as the six codons for arginine or serine, as set forth in Table I, and also refers to codons that encode biologically equivalent amino acids.

It will also be understood that amino acid and nucleic acid sequences may include additional residues, such as additional N- or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzyme activity is concerned. The addition of terminal sequences particularly applies to nucleic acid sequences which may, for example, include various non-coding sequences flanking either of the 5' or 3' portions of the coding region or may include various internal sequences, which are known to occur within genes. In particular, the amino acid sequence of the HAS gene in eukaryotes appears to be 40% larger than that found in prokaryotes.

Allowing for the degeneracy of the genetic code as well as conserved and semi-conserved substitutions, sequences which have between about 40% and about 80%; or more preferably, between about 80% and about 90%; or even more preferably, between about 90% and about 99%; of nucleotides which are identical to the nucleotides of SEQ ID NO:1 will be sequences which are "essentially as set forth in SEQ ID NO:1". Sequences which are essentially the same as those set forth in SEQ ID NO:1 may also be functionally defined as sequences which are capable of hybridizing to a nucleic acid segment containing the complement of SEQ ID NO:1 under standard or less stringent hybridizing conditions. Suitable standard hybridization conditions will be well known to those of skill in the art and are clearly set forth herein.

The term "standard hybridization conditions" as used herein, is used to describe those conditions under which substantially complementary nucleic acid segments will form standard Watson-Crick base-pairing. A number of factors are known that determine the specificity of binding or hybridization, such as pH, temperature, salt concentration, the presence of agents, such as formamide and dimethyl sulfoxide, the length of the segments that are hybridizing, and the like. When it is contemplated that shorter nucleic acid segments will be used for hybridization, for example fragments between about 14 and about 100 nucleotides, salt and temperature preferred conditions for hybridization will include 1.2–1.8×HPB at 40–50° C.

Naturally, the present invention also encompasses DNA segments which are complementary, or essentially complementary, to the sequence set forth in SEQ ID NO:1. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular nucleic acid and amino acid sequences of SEQ ID NO:1 and 2. Recombinant vectors and isolated DNA segments may therefore variously include the HAS coding regions themselves, coding regions bearing selected alterations or modifications in the basic coding region, or they may encode larger polypeptides which nevertheless include HAS-coding regions or may encode biologically functional equivalent proteins or peptides which have variant amino acids sequences.

For instance, we have found, characterized, and purified hyaluronate synthase in two other systems: (1) the gram-negative bacteria *Pasturella multocida* (SEQ ID NO:9); and (2) chlorella virus PBCV-1 (SEQ ID NOS:7 and 8). The presence of hyaluronan synthase in these two systems and our ability to purify and use the hyaluronan synthase from these two different systems indicates our ability to purify and isolate nucleic acid sequences encoding enzymatically active hyaluronan synthase.

The capsule of Carter Type A *P. multocida* (SEQ ID NO:9) was long suspected of containing hyaluronic acid-HA. Characterization of the HA synthase of *P. multocida* led to interesting enzymological differences between it and the seHAS and spHAS proteins.

*P. multocida* cells produce a readily visible extracellular HA capsule, and since the two streptococcal HASs are membrane proteins, membrane preparations of the fowl cholera pathogen were tested. In early trials, crude membrane fractions derived from ultrasonication alone possessed very low levels of UDP-GlcNAc-dependent UDP-[$^{14}$C]GlcA incorporation into HA[~0.2 pmol of GlcA transfer (μg of proteins)$^{-1}$h$^{-1}$] when assayed under conditions similar to those for measuring streptococcal HAS activity. The enzyme from *E. coli* with the recombinant hasA plasmid was also recalcitrant to isolation at first. These results were in contrast to the easily detectable amounts obtained from *Streptococcus* by similar methods.

An alternative preparation protocol using ice-cold lysozyme treatment in the presence of protease inhibitors in conjunction with ultrasonication allowed the substantial recovery of HAS activity from both species of Gram-negative bacteria. Specific activities for HAS of 5–10 pmol of GlcA transferred (μg of protein)$^{-1}$h$^{-1}$ were routinely obtained for crude membranes of wild-type *P. multocida* with the new method. In the absence of UDP-GlcNAc, virtually no radioactivity (<1% of identical assay with both sugar precursors) from UDP-[$^{14}$C]GlcA was incorporated into higher molecular weight material. Membranes prepared from the acapsular mutant, TnA, possessed no detectable HAS activity when supplemented with both sugar nucleotide precursors (data not shown). Gel-filtration analysis using a Sephacryl S-200 column indicates that the molecular mass of the majority of the $^{14}$C-labeled product synthesized in vitro is $\geqq 8\times10^4$ Da since the material elutes in the void volumes, such a value corresponds to a HA molecule composed of at least 400 monomers. This product is sensitive to *Streptomyces* hyaluronidase digestion but resistant to protease treatment.

The parameters of the HAS assay were varied to maximize incorporation of UDP-sugars into polysaccharide by *P. multocida* membranes. Streptococcal spHAS requires $Mg^{2+}$ and therefore this metal ion was included in the initial assays of *P. multocida* membranes. The *P. multocida* HAS (pmHAS) was relatively active from pH 6.5 to 8.6 in Tris-type buffers with an optimum at pH 7. The HAS activity was linear with respect to the incubation time at neutral pH for at least 1 h. The pmHAS was apparently less active at higher ionic strengths because the addition of 100 mM NaCl to the reaction containing 50 mM Tris, pH 7, and 20 mM $MgCl_2$ reduced sugar incorporation by ~50%.

The metal ion specificity of the pmHAS was assessed at pH 7. Under metal-free conditions in the presence of EDTA, no incorporation of radiolabeled precursor into polysaccharide was detectable (<0.5% of maximal signal). $Mn^{2+}$ gave the highest incorporation rates at the lowest ion concentrations for the tested metals (Mg, Mn, Co, Cu, and Ni). $Mg^{2+}$ gave about 50% of the $Mn^{2+}$ stimulation but at 10-fold higher concentrations. $Co^{2+}$ or $Ni^{2+}$ at 10 mM supported lower levels of activity (20% or 9%, respectively, of 1 mM $Mn^{2+}$ assays), but membranes supplied with 10 mM $Cu^{2+}$ were inactive. Indeed, mixing 10 mM $Cu^{2+}$ and 20 mM$^{2+}$ Mg2+ with the membrane preparation resulted in almost no incorporation of label into polysaccharide (<0.8% of Mg only value).

Initial characterization of the pmHAS was performed in the presence of $Mg^{2+}$. The binding affinity of the enzyme for its sugar nucleotide precursors was assessed by measuring the apparent $K_M$ value. Incorporation of [$^{14}$C]GlcA or [$^{3}$H]GlcNAc into polysaccharide was monitored at varied concentrations of UDP-GlcNAc or UDP-GlcA, respectively. In $Mg^{2+}$-containing buffers, the apparent $K_M$ values of ~20 μM for UDP-GlcA and ~75 μM for UDP-GlcNAc were determined utilizing Hanes-Woolf plots ([S]/v versus [S]) of the titration data. The $V_{max}$ values for both sugars were the same because the slopes, corresponding to $1/V_{max}$, of the Hanes-Woolf plots were equivalent. In comparison to results from assays with $Mg^{2+}$, the $K_M$ value for UDP-GlcNAc was increased by about 25–50% to ~105 μM and the $V_{max}$ increased by a factor of 2–3-fold in the presence of $Mn^{2+}$.

The HA synthase enzymes from either *P. multocida*, *S. equisimilis*, or *S. pyogenes* utilizes UDP-sugars, but they possess somewhat different kinetic optima with respect to pH and metal ion dependence and $K_M$ values. The enzymes are most active at pH 7; however, the pmHAS reportedly displays more activity at slightly acidic pH and is relatively inactive above pH 7.4. The pmHAS utilizes $Mn^{2+}$ more efficiently than $Mg^{2+}$ under the in vitro assay conditions, but the identity of the physiological metal cofactor in the bacterial cell is unknown. In comparison, in previous studies with the streptococcal enzyme, $Mg^{2+}$ was much better than $Mn^{2+}$ but the albeit smaller effect of $Mn^{2+}$ was maximal at ~10-fold lower concentrations than the optimal $Mg^{2+}$ concentration. The pmHAS apparently binds the UDP-sugars more tightly than spHAS. The measured KM values for the pmHAS in crude membranes are about 2–3-fold lower for each substrate than those obtained from the HAS found in streptococcal membranes: 50 or 39 μM for UDP-GlcA and 500 or 150 μM for UDP-GlcNAc, respectively.

By kinetic analyses, the $V_{max}$ of the pmHAS was 2–3-fold higher in the presence of $Mn^{2+}$ than $Mg^{2+}$, but the UDP-GlcNAc $K_M$ value was increased slightly in assays with the former ion. This observation of apparent lowered affinity suggests that the increased polymerization rate was not due to better binding of the $Mn^{2+}$ ion/sugar nucleotide complex to the enzyme active site(s). Therefore, it is possible that $Mn^{2+}$ enhances some other reaction step, alters another site/structure of the enzyme, or modifies the phospholipid membrane environment. The gene sequence and the protein sequence of pmHAS are shown in SEQ ID NO:9.

Chlorella virus PBCV-1 encodes a functional glycosyltransferase that can synthesize a polysaccharide, hyaluronan [hyaluronic acid, HA]. This finding is contrary to the general observation that viruses either: (a) utilize host cell glycosyltransferases to create new carbohydrate structures, or (b) accumulate host cell glycoconjugates during virion maturation. Furthermore, HA has been generally regarded as restricted to animals and a few of their virulent bacterial pathogens. Though many plant carbohydrates have been characterized, neither HA nor a related analog has previously been detected in cells of plants or protists.

The vertebrate HAS enzymes (DG42, HAS1, HAS2, HAS3) and streptococcal HasA enzymes (spHAS and seHAS) have several regions of sequence similarity. While sequencing the double-stranded DNA genome of virus PBCV-1 [*Paramecium bursaria* chlorella virus], an ORF [open reading frame], A98R (Accession #442580), encoding a 567 residue protein with 28 to 33% amino acid identity to the various HASs was discovered. This protein is designated cvHAS (chlorella virus HA synthase). The gene sequence encoding PBCV-1 and its protein sequence are shown in SEQ ID NOS:7 and 8.

PBCV-1 is the prototype of a family (Phycodnarviridae) of large (175–190 nm diameter) polyhedral, plaque-forming viruses that replicate in certain unicellular, eukaryotic chlorella-like green algae. PBCV-1 virions contain at least 50 different proteins and a lipid component located inside the outer glycoprotein capsid. The PBCV-1 genome is a linear, nonpermuted 330-kb dsDNA molecule with covalently closed hairpin ends.

Based on its deduced amino acid sequence, the A98R gene product should be an integral membrane protein. To test this hypothesis, recombinant A98R was produced in *Escherichia coli* and the membrane fraction was assayed for HAS activity. UDP-GlcA and UDP-GlcNAc were incorporated into the polysaccharide by the membrane fraction derived from cells containing the A98R gene on a plasmid, pCVHAS, (average specific activity 2.5 pmoles GlcA transfer/μg protein/min) but not by samples from control cells (<0.001 pmoles GlcA transfer/μg protein/min). No activity was detected in the soluble fraction of cells transformed with pCVHAS. UDP-GlcA and UDP-GlcNAc were simultaneously required for polymerization. The activity was optimal in Hepes buffer at pH 7.2 in the presence of 10 mM $MnCl_2$, whereas no activity was detected if the metal ion was omitted. $Mg^{2+}$ and $Co^{2+}$ were ~20% as effective as $Mn^{2+}$ at similar concentrations. The pmHAS has a similar metal requirement, but other HASs prefer $Mg^{2+}$.

The recombinant A98R enzyme synthesized a polysaccharide with an average molecular weight of $3-6\times10^6$ Da which is smaller than that of the HA synthesized by recombinant spHAS or DG42 xlHAS in vitro (~$10^7$ Da and ~$5-8\times10^6$ Da, respectively; 13, 15). The polysaccharide was completely degraded by *Streptomyces hyaluroniticus* HA lyase, an enzyme that depolymerizes HA, but not structurally related glycosaminoglycans such as heparin and chondroitin.

PBCV-1 infected chlorella cells were examined for A98R gene expression. A ~1,700-nucleotide A98R transcript appeared at ~15 min post-infection and disappeared by 60 min after infection indicating that A98R is an early gene. Consequently, membrane fractions from uninfected and PBCV-1 infected chlorella cells were assayed at 50 and 90 min post-infection for HAS activity. Infected cells, but not uninfected cells, had activity. Like the bacterially derived recombinant A98R enzyme, radiolabel incorporation from UDP-[$^{14}$C]GlcA into polysaccharide depended on both $Mn^{2+}$ and UDP-GlcNAc. This radiolabeled produce was also degraded by HA lyase. Disrupted PBCV-1 virions had no HAS activity.

PBCV-1 infected chlorella cells were analyzed for HA polysaccharide using a highly specific $^{125}$I-labeled HA-binding protein. Extracts from cells at 50 and 90 min post-infection contained substantial amounts of HA, but not extracts from uninfected algae or disrupted PBCV-1 virions. The labeled HA-binding protein also interacted with intact infected cells at 50 and 90 min post-infection, but not healthy cells. Therefore, a considerable portion of the newly synthesized HA polysaccharide was immobilized at the outer cell surface of the infected algae. The extracellular HA does not play any obvious role in the interaction between the virus and its algal host because neither plaque size nor plaque number was altered by including either testicular hyaluronidase (465 units/ml) or free HA polysaccharide (100 μg/ml) in the top agar of the PBCV-1 plaque assay.

The PBCV-1 genome also has additional genes that encode for an UDP-Glc dehydrogenase (UDP-Glc DH) and a glutamine:fructose-6-phosphate aminotransferase (GFAT). UDP-Glc DH converts UDP-Glc into UDP-GlcA, a required precursor for HA biosynthesis. GFAT converts fructose-6-phosphate into glucosamine-6-phosphate, an intermediate in the UDP-GlcNAc metabolic pathway. Both of these PBCV-1 genes, like the A98R HAS, are expressed early in infection and encode enzymatically active proteins. The presence of multiple enzymes in the HA biosynthesis pathway indicates that HA production must serve an important function in the life cycle of the chlorella viruses.

HA synthases of *Streptococcus*, vertebrates, and PBCV-1 possess many motifs of 2 to 4 residues that occur in the same relative order. These conserved motifs probably reflect domains crucial for HA biosynthesis as shown in FIG. 2. The protein sequences of Group C seHAS, Group A spHAS, murine HAS1, HAS2, HAS3, and frog HAS are shown aligned in FIG. 2. The alignment of FIG. 2 was accomplished using the DNASIS multiple alignment program. Residues in seHAS identical in other known HAS family members (including human HAS1 and 2, not shown) are denoted by shading and asterisks. The amino acids indicated by dots are conserved in all members of the larger β-glycosyl transferase family. The diamond symbol indicates the highly conserved cysteine residue that may be critical for enzyme activity. The approximate mid-points of predicted membrane domains MD1 through MD7 are indicated with arrows. X1 indicates *Xeopus laevis*, and MM denotes *Mus musculis*.

Regions of similarity between HASs and other enzymes that synthesize β-linked polysaccharides from UDP-sugar precursors are also being discovered as more glycosyltransferases are sequenced. Examples include bacterial cellulose synthase, fungal and bacterial chitin synthases, and the various HASs. The significance of these similar structural motifs will become more apparent as the three-dimensional structures of glycosyltransferases accumulate.

Figure 3:
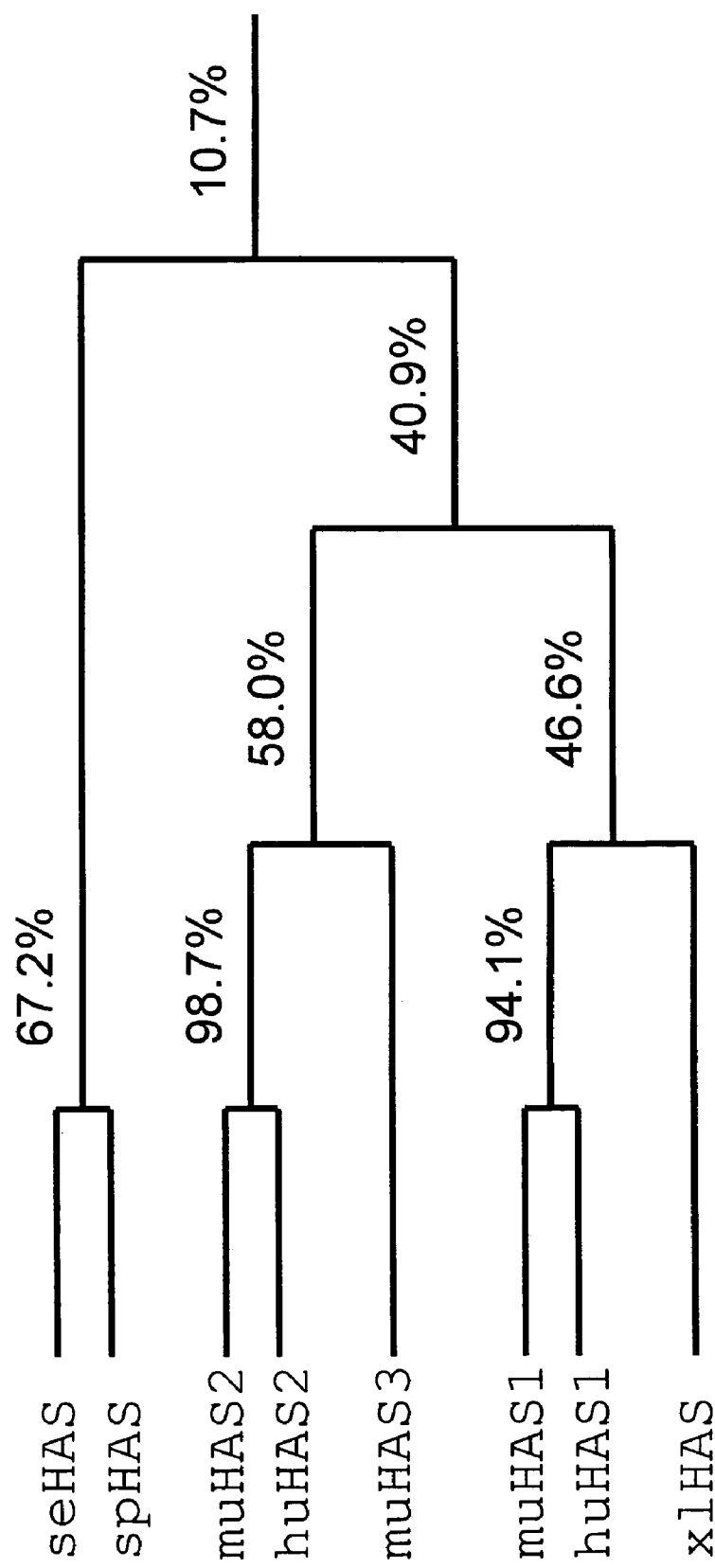
FIG. 3 figuratively depicts evolutionary relationships among some of the known hyaluronan synthases.

FIG. 3 depicts the evolutionary relationships among the known hyaluronan synthase. The phylogenetic tree of FIG. 3 was generated by the Higgins-Sharp algorithm using the DNAsis multiple alignment program. The calculated matching percentages are indicated at each branch of the dendrogram.

The DNA segments of the present invention encompass biologically functional equivalent HAS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HAS protein or to test HAS mutants in order to examine HA synthase activity at the molecular level.

Also, specific changes to the HAS coding sequence can result in the production of HA having a modified size distribution or structural configuration. One of ordinary skill in the art would appreciate that the HAS coding sequence can be manipulated in a manner to produce an altered hyaluronate synthase which in turn is capable of producing hyaluronic acid having differing polymer sizes and/or functional capabilities. For example, the HAS coding sequence may be altered in such a manner that the hyaluronate synthase has an altered sugar substrate specificity so that the hyaluronate synthase creates a new hyaluronic acid-like polymer incorporating a different structure such as a previously unincorporated sugar or sugar derivative. This newly incorporated sugar could result in a modified hyaluronic acid having different functional properties, a hyaluronic acid having a smaller or larger polymer size/molecular weight, or both. As will be appreciated by one of ordinary skill in the art given the HAS coding sequences, changes and/or substitutions can be made to the HAS coding sequence such that these desired property and/or size modifications can be accomplished. Table II lists sugar nucleotide specificity and magnesium ion requirement of recombinant seHAS.

TABLE II

Sugar nucleotide specificity and Magnesium ion requirement of recombinant seHAS

| | HA Synthesis* | |
|---|---|---|
| Second Sugar nucleotide present (µM) | UDP-[$^{14}$C]GlcA dpm (%) | UDP-[$^3$H]GlcNAc dpm (%) |
| None | 90 (2.1%) | 8 (1.2%) |
| UDP-GlcNAc (300) | 4134 (100%) | — |
| UDP-GlcA (120) | — | 635 (100%) |
| UDP-Glc (160) | 81 (1.9%) | 10 (1.5%) |
| UDP-GalNAc (280) | 74 (1.7%) | 19 (2.9%) |
| UDP-GalA (150) | 58 (1.4%) | 19 (2.9%) |
| UDP-GlcNAc + EDTA | 31 (0.7%) | — |
| UDP-GlcA + EDTA | — | 22 (3.4%) |

*Membranes (324 ng protein) were incubated at 37° C. for 1 h with either 120 µM UDP-[$^{14}$C] GlcA (2.8 × 10$^4$ dpm) or 300 µM UDP-[$^3$H]GlcNAc (2 × 10$^4$ dpm). The radiolabeled sugar nucleotide was used in the presence of the indicated second nonlabeled sugar nucleotide. HA synthase activity was determined as described in the application.

The term "modified structure" as used herein denotes a hyaluronic acid polymer containing a sugar or derivative not normally found in the naturally occurring HA polysaccharide. The term "modified size distribution" refers to the synthesis of hyaluronic acid molecules of a size distribution not normally found with the native enzyme; the engineered size could be much smaller or larger than normal.

Various hyaluronic acid products of differing size have application in the areas of drug delivery and the generation of an enzyme of altered structure can be combined with a hyaluronic acid of differing size. Applications in angiogenesis and wound healing are potentially large if hyaluronic acid polymers of about 20 monosaccharides can be made in good quantities. Another particular application for small hyaluronic acid oligosaccharides is in the stabilization of recombinant human proteins used for medical purposes. A major problem with such proteins is their clearance from the blood and a short biological half life. One present solution to this problem is to couple a small molecule shield that prevents the protein from being cleared from the circulation too rapidly. Very small molecular weight hyaluronic acid is well suited for this role and would be nonimmunogenic and biocompatible. Larger molecular weight hyaluronic acid attached to a drug or protein may be used to target the reticuloendothelial cell system which has endocytic receptors for hyaluronic acid.

One of ordinary skill in the art given this disclosure would appreciate there are several ways in which the size distribution of the hyaluronic acid polymer made by the hyaluronate synthase could be regulated to give different sizes. First, the kinetic control of product size can be altered by decreasing temperature, decreasing time of enzyme action and by decreasing the concentration of one or both sugar nucleotide substrates. Decreasing any or all of these variables will give lower amounts and smaller sizes of hyaluronic acid product. The disadvantages of these approaches are that the yield of product will also be decreased and it may be difficult to achieve reproducibility from day to day or batch to batch.

Secondly, the alteration of the intrinsic ability of the enzyme to synthesize a large hyaluronic acid product. Changes to the protein can be engineered by recombinant DNA technology, including substitution, deletion and addition of specific amino acids (or even the introduction of prosthetic groups through metabolic processing). Such changes that result in an intrinsically slower enzyme could then allow more reproducible control of hyaluronic acid size by kinetic means. The final hyaluronic acid size distribution is determined by certain characteristics of the enzyme, that rely on particular amino acids in the sequence. Among the 20% of residues absolutely conserved between the streptococcal enzymes and the eukaryotic hyaluronate synthases, there is a set of amino acids at unique positions that control or greatly influence the size of the hyaluronic acid polymer that the enzyme can make. Specific changes in any of these residues can produce a modified HAS that produces an HA product having a modified size distribution. Engineered changes to seHAS, spHAS, pmHAS, or cvHAS that decrease the intrinsic size of the hyaluronic acid that the enzyme can make before the hyaluronic acid is released, will provide powerful means to produce hyaluronic acid product of smaller or potentially larger size than the native enzyme.

Finally, larger molecular weight hyaluronic acid made be degraded with specific hyaluronidases to make lower molecular weight hyaluronic acid. This practice, however, is very difficult to achieve reproducibility and one must meticulously repurify the hyaluronic acid to remove the hyaluronidase and unwanted digestion products.

Figure 4:
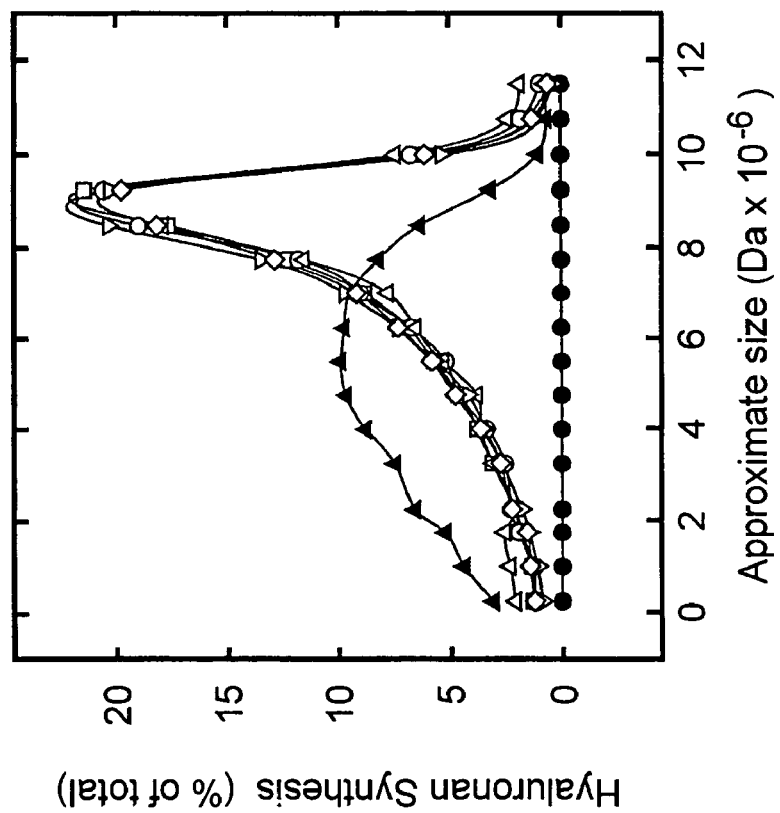
FIG. 4 depicts the HA size distribution produced by various engineered Streptococcal HAS enzymes.

As shown in FIG. 4, hyaluronan synthase can be engineered to produce hyaluronic acid polymers of different size, in particular smaller, than the normal wildtype enzyme. The figure shows the distribution of HA sizes (in millions of Daltons, a measure of molecular weight) for a series of spHAS enzymes, each of which was engineered by site directed mutagenesis to have a single amino acid change from the native enzyme. Each has a different Cysteine residue replaced with Alanine. The cluster of five curves with open symbols represent the following spHAS proteins: wildtype, C124A, C261A, C366A, and C402A. The filled circles represent the poorly expressed C225A protein which is only partially active.

The filled triangles is the C280A spHAS protein, which is found to synthesize a much smaller range of HA polymers than the normal enzyme or the other variants shown. This reduction to practice shows that it is feasible to engineer the hyaluronate synthase enzyme to synthesize a desired range of HA product sizes. The seHAS, pmHAS, and cvHAS genes encoding hyaluronate synthase can also be manipulated by site directed mutagenesis to produce an enzyme which synthesizes a desired range of HA product sizes.

Structurally modified hyaluronic acid is no different conceptually than altering the size distribution of the hyaluronic acid product by changing particular amino acids in the desired HAS or the spHAS. Derivatives of UDP-GlcNAc, in which the N-acetyl group is missing UDP-GlcN or replaced with another chemically useful group, are expected to be particularly useful. The strong substrate specificity must rely on a particular subset of amino acids among the 20% that are conserved. Specific changes to one or more of these residues creates a functional synthase that interacts less specifically with one or more of the substrates than the native enzyme. This altered enzyme could then utilize alternate natural or special sugar nucleotides to incorporate sugar derivatives designed to allow different chemistries to be employed for the following purposes: (i) covalently coupling specific drugs, proteins, or toxins to the structurally modified hyaluronic acid for general or targeted drug delivery, radiological procedures, etc. (ii) covalently cross linking the hyaluronic acid itself or to other supports to achieve a gel, or other three dimensional biomaterial with stronger physical properties, and (iii) covalently linking hyaluronic acid to a surface to create a biocompatible film or monolayer.

Bacteria can also be engineered to produce hyaluronic acid. For instance, we have created strains of B. subtilis containing the spHAS gene, as well as the gene for one of the sugar nucleotide precursors. We chose this bacteria since it is frequently used in the biotech industry for the production of products for human use. These bacteria were intended as first generation prototypes for the generation of a bacterium able to produce hyaluronic acid in larger amounts than presently available using a wild type natural strain. We put in multiple copies of these genes.

For example, three Bacillus subtilis strains were constructed to contain one or both of the Streptococcus pyogenes genes for hyaluronan synthase (spHAS) and UDP-glucose dehydrogenase, the results of which are shown in Table II-B. Based on a sensitive commercial radiometre assay to detect and quantitate HA, it was determined that the strain with both genes (strain #3) makes and secretes HA into the medium. The parent strain or the strain with just the dehydrogenase gene (strain #1) does not make HA. Strain #2, which contains just the spHAS gene alone makes HA, but only 10% of what strain #3 makes. Agarose gel electrophoresis showed that the HA secreted into the medium by strain #3 is very high molecular weight.

TABLE II-B

| Strain Number | Cells | Medium(*) | Strain with genes | Cell density ($A_{600}$) |
|---|---|---|---|---|
| | (μg HA per ml of culture) | | | |
| 1 | 0 | 0 | hasB | 4.8 |
| 2 | 4 | 35 | SpHAS | 3.9 |
| 3 | =>10 | >250 | SpHAS + hasB | 3.2 |

These experiments used the streptococcal promoters normally found with these genes to drive protein expression. It is expected that the construction of strains with the spHAS or seHAS reading frame under control of a B. subtilis promoter would yield even more superior results. The vector used is a Gram positive/E Coli shuttle vector that has a medium copy number in B. subtilis and a gene for erythromycin resistance (enabling resistence to 8 μg/ml in B. subtilis or 175 μg/ml in E. coli). The B. subtilis host strain used is 1A1 from BGSC, which has a tryptophan requirement but otherwise is wildtype, and can sporulate. Cell growth and HA production was in Spizizens Minimal Media plus tryptophan, glucose, trace elements and erthromycin (8 μg/ml). Growth was at 32 degrees Celsius with vigorous agitation until the medium was exhausted (~36 hours).

This demonstrates that these bioengineered cells, which would not normally make hyaluronic acid, became competent to do so when they are transformed with the spHAS gene. The seHAS would also be capable of being introduced into a non-hyaluronic acid producing bacteria to create a bioengineered bacterial strain capable of producing hyaluronic acid.

Figure 5:
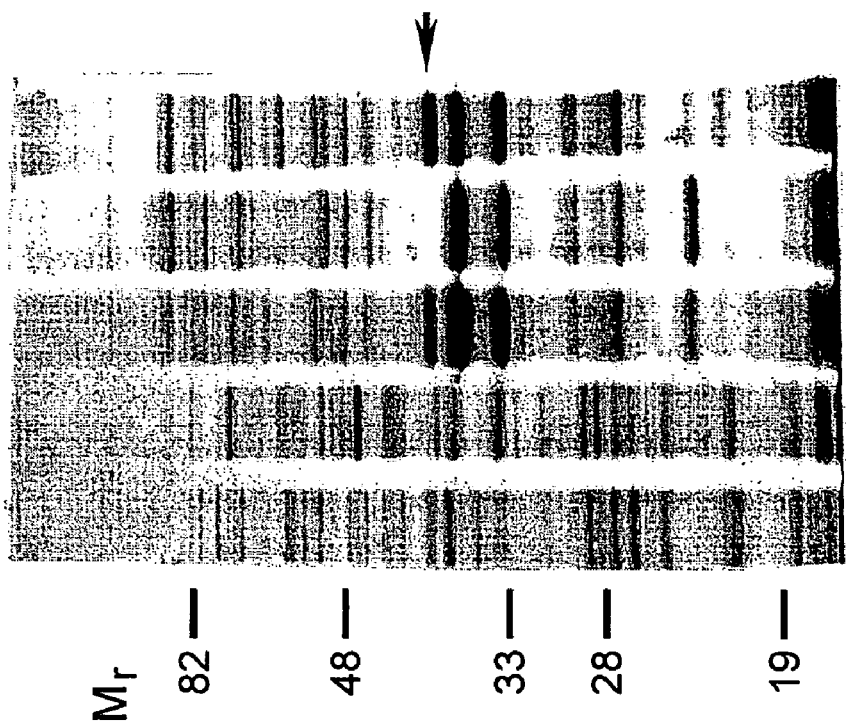
FIG. 5 figuratively depicts the overexpression of recombinant seHAS and spHAS in *E. coli*.

A preferred embodiment of the present invention is a purified composition comprising a polypeptide having an amino acid sequence in accordance with SEQ ID NO:2. The term "purified" as used herein, is intended to refer to an HAS protein composition, wherein the HAS protein or appropriately modified HAS protein (e.g., containing a $[HIS]_6$ tail) is purified to any degree relative to its naturally-obtainable state, i.e., in this case, relative to its purity within a prokaryotic cell extract. HAS protein may be isolated from *Streptococcus, Pasturella*, chlorella virus, patient specimens, recombinant cells, infected tissues, isolated subpopulation of tissues that contain high levels of hyaluronate in the extracellular matrix, and the like, as will be known to those of skill in the art, in light of the present disclosure. For instance, the recombinant seHAS or spHAS protein makes up approximately 10% of the total membrane protein of *E. coli*. A purified HAS protein composition therefore also refers to a polypeptide having the amino acid sequence of SEQ ID NO:2, free from the environment in which it may naturally occur (FIG. 5).

Turning to the expression of the seHAS gene whether from genomic DNA, or a cDNA, one may proceed to prepare an expression system for the recombinant preparation of the HAS protein. The engineering of DNA segment(s) for expression in a prokaryotic or eukaryotic system may be performed by techniques generally known to those of skill in recombinant expression.

HAS may be successfully expressed in eukaryotic expression systems, however, the inventors aver that bacterial expression systems can be used for the preparation of HAS for all purposes. It is believed that bacterial expression will ultimately have advantages over eukaryotic expression in terms of ease of use, cost of production, and quantity of material obtained thereby.

Figure 6:
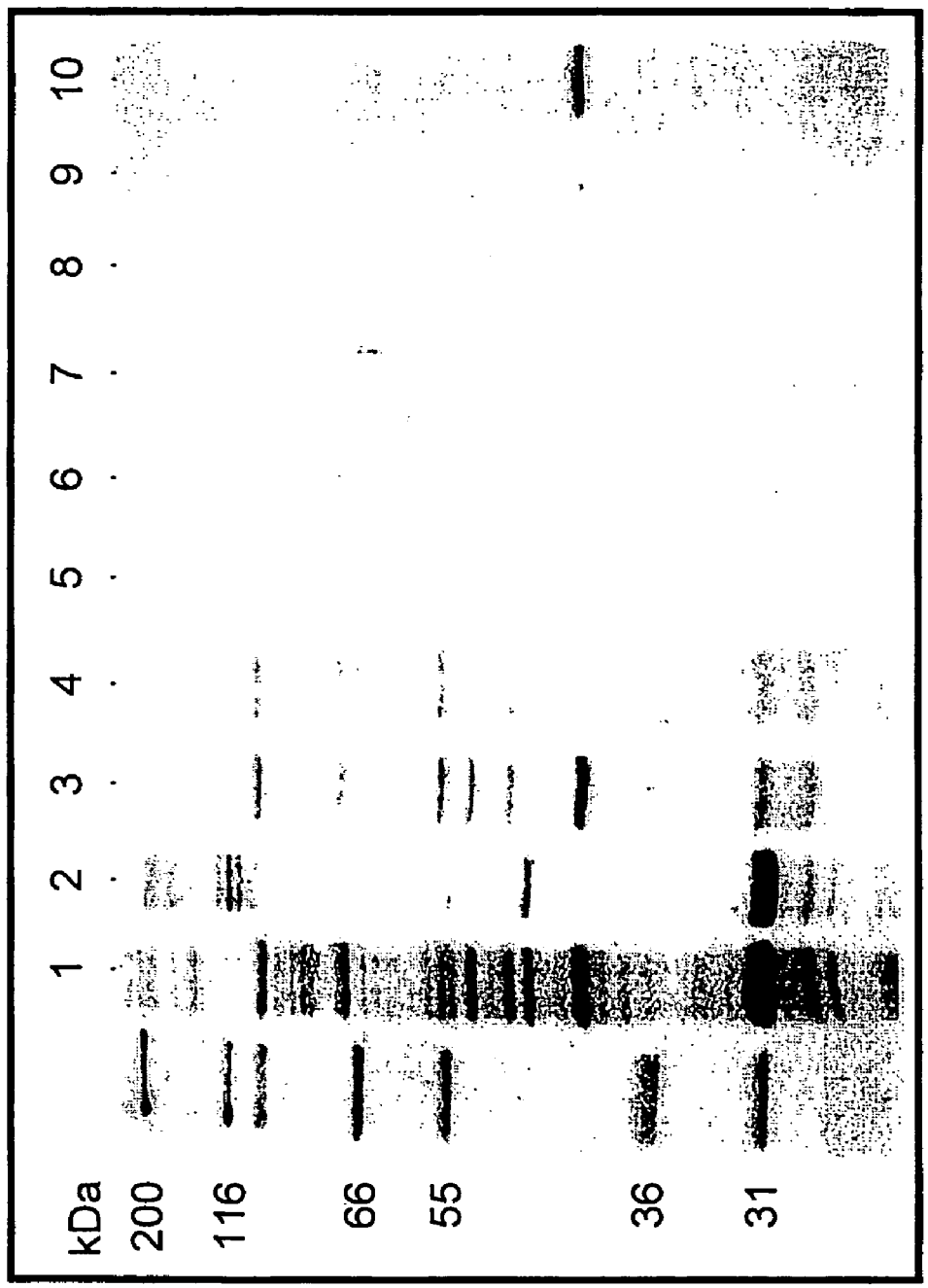
FIG. 6 depicts purification of streptococcal HA synthase.

The purification of streptococcal hyaluronan synthase (seHAS and spHAS) is shown in Table III and FIG. 6. Fractions from various stages of the purification scheme were analyzed by SDS-PAGE on a 12.5% gel, which was then stained with Coomassie Brilliant Blue R-250. Lanes: molecular weight markers; 1, whole *E. coli* membranes containing the recombinant seHAS-H6; 2, insoluble fraction after detergent solubilization of membranes; 3, detergent solubilized fraction; 4, flow-through from the Ni-NTA chromatography resin; 5–9, five successive washes of the column (two column volumes each); 10, the eluted pure HA synthase which is a single band.

TABLE III

| Step | Total Protein (ug) | Specific Activity (mmol/ug/hr.) | Total Activity (nmol UDP-GlcA) | Yield (%) | Purification (–fold) |
|---|---|---|---|---|---|
| Membranes | 3690 | 1.0 | 3649 | 100 | 1.0 |
| Extract | 2128 | 2.2 | 4725 | 129 | 2.2 |
| Affinity Column | 39 | 13 | 500 | 14 | 13.1 |

It is proposed that transformation of host cells with DNA segments encoding HAS will provide a convenient means for obtaining a HAS protein. It is also proposed that cDNA, genomic sequences, and combinations thereof, are suitable for eukaryotic expression, as the host cell will, of course, process the genomic transcripts to yield functional mRNA for translation into protein.

Another embodiment of the present invention is a method of preparing a protein composition comprising growing a recombinant host cell comprising a vector that encodes a protein which includes an amino acid sequence in accordance with SEQ ID NO:2 or functionally similar with conserved or semi-conserved amino acid changes. The host cell will be grown under conditions permitting nucleic acid expression and protein production followed by recovery of the protein so produced. The production of HAS and ultimately HA, including the host cell, conditions permitting nucleic acid expression, protein production and recovery will be known to those of skill in the art in light of the present disclosure of the seHAS gene, and the seHAS gene protein product HAS, and by the methods described herein.

Preferred hosts for the expression of hyaluronic acid are prokaryotes, such as *S. equisimilis*, and other suitable members of the *Streptococcus* species. However, it is also known that HA may be synthesized by heterologous host cells expressing recombinant HA synthase, such as species members of the *Bacillus, Enterococcus*, or even *Escherichia* genus. A most preferred host for expression of the HA synthase of the present invention is a bacteria transformed with the HAS gene of the present invention, such as *Lactococcus* species, *Bacillus subtilis* or *E. coli*.

Figure 7:
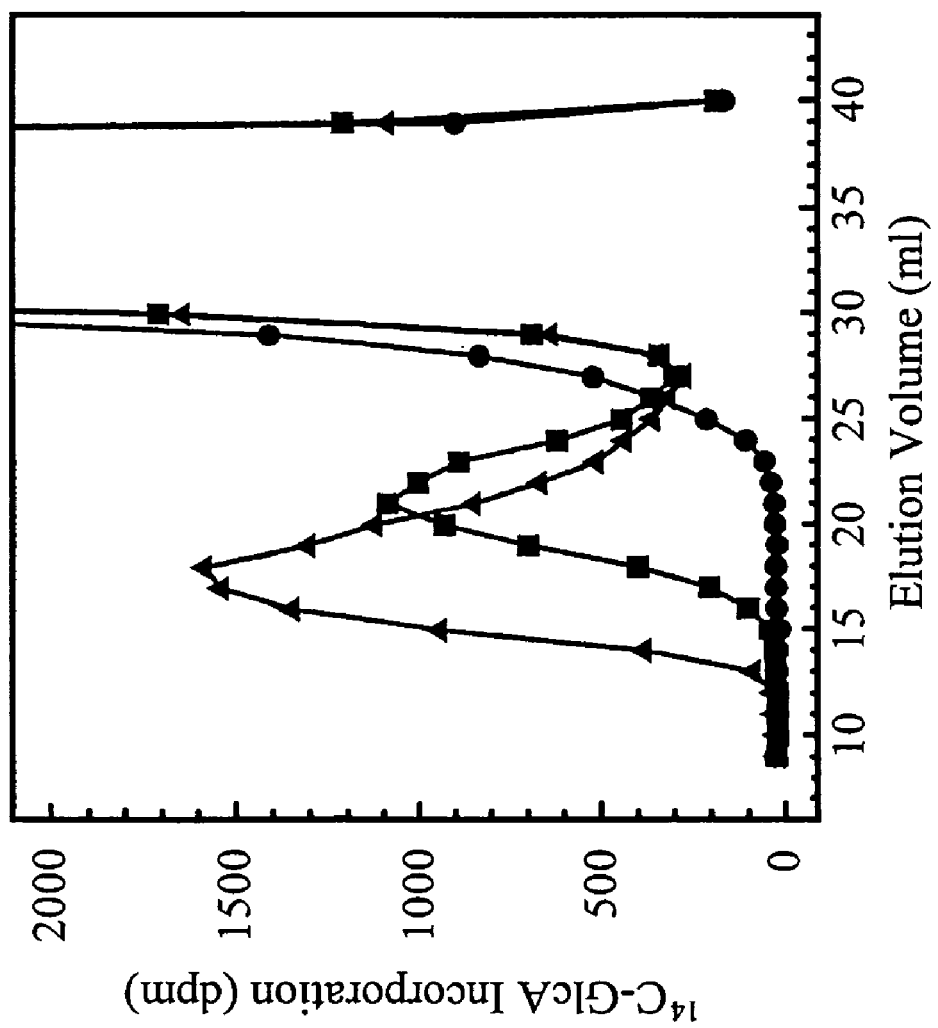
FIG. 7 depicts a gel filtration analysis of HA synthesized by recombinant streptococcal HAS expressed in yeast membranes.

It is similarly believed that almost any eukaryotic expression system may be utilized for the expression of HAS e.g., baculovirus-based, glutamine synthase-based, dihydrofolate reductase-based systems, SV40 based, adenovirus-based, cytomegalovirus-based, yeast-based, and the like, could be employed. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter. Also, *Saccharomyces cevevisiae* yeast expression vector systems, such as pYES2, will also produce HAS under control of the GAL promoter as shown in FIG. 7. FIG. 7 shows that the spHAS enzyme was produced in recombinant yeast using the pYES2 plasmid. When supplied with UDP-GlcA and UDP-GlcNAc, the enzyme makes high molecular weight HA.

Where eukaryotic expression is contemplated, one will also typically desire to incorporate into the transcriptional unit which includes the HAS gene or DNA, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of HAS in accordance herewith. Examples of preferred cell lines for expressing HAS cDNA of the present invention include cell lines typically employed for eukaryotic expression such as 239, AtT-20, HepG2, VERO, HeLa, CHO, WI 38, BHK, COS-7, RIN and MDCK cell lines. This will generally include the steps of providing a recombinant host bearing the recombinant DNA segment encoding the HAS enzyme and capable of expressing the enzyme; culturing the recombinant host in media under conditions that will allow for transcription of the cloned HAS gene or cDNA and appropriate for the production of the hyaluronic acid;

and separating and purifying the HAS enzyme or the secreted hyaluronic acid from the recombinant host.

Generally, the conditions appropriate for expression of the cloned HAS gene or cDNA will depend upon the promoter, the vector, and the host system that is employed. For example, where one employs the lac promoter, one will desire to induce transcription through the inclusion of a material that will stimulate lac transcription, such as isopropylthiogalactoside. For example, the cloned seHAS gene of the present invention is expressed as a $HIS_6$ containing protein in *E. coli* as shown in FIG. 5. Where other promoters are employed, different materials may be needed to induce or otherwise up-regulate transcription.

FIG. 5 depicts the overexpression of recombinant seHAS and spHAS in *E. coli*. Membrane proteins (5 mg per lane) were fractionated by SDS-PAGE using a 10% (w/v) gel under reducing conditions. The gel was stained with Coomassie blue R-250, photographed, scanned, and quantitated using a molecular dynamics personal densitometer (model PDSI P60). The position of HA synthase is marked by the arrow. Lane A is native spHAS (Group A); Lane C is native seHAS; Lane E is recombinant seHAS; Lane P is recombinant spHAS; Lane V is vector alone. Standards used were Bio-rad low Mr and shown in kDa.

In addition to obtaining expression of the synthase, one will preferably desire to provide an environment that is conducive to HA synthesis by including appropriate genes encoding enzymes needed for the biosynthesis of sugar nucleotide precursors, or by using growth media containing substrates for the precursor-supplying enzymes, such as N-acetylglucosamine or glucosamine (GlcNAc or $GlcNH_2$) and glucose (Glc).

One may further desire to incorporate the gene in a host which is defective in the enzyme hyaluronidase, so that the product synthesized by the enzyme will not be degraded in the medium. Furthermore, a host would be chosen to optimize production of HA. For example, a suitable host would be one that produced large quantities of the sugar nucleotide precursors to support the HAS enzyme and allow it to produce large quantities of HA. Such a host may be found naturally or may be made by a variety of techniques including mutagenesis or recombinant DNA technology. The genes for the sugar nucleotide synthesizing enzymes, particularly the UDP-Glc dehydrogenase required to produce UDP-GlcA, could also be isolated and incorporated in a vector along with the HAS gene or cDNA. A preferred embodiment of the present invention is a host containing these ancillary recombinant gene or cDNAs and the amplification of these gene products thereby allowing for increased production of HA.

The means employed for culturing of the host cell is not believed to be particularly crucial. For useful details, one may wish to refer to the disclosure of U.S. Pat. Nos. 4,517,295; 4,801,539; 4,784,990; or 4,780,414; all incorporated herein by reference. Where a prokaryotic host is employed, such as *S. equisimilis*, one may desire to employ a fermentation of the bacteria under anaerobic conditions in $CO_2$-enriched broth growth media. This allows for a greater production of HA than under aerobic conditions. Another consideration is that streptococcal cells grown anaerobically do not produce pyrogenic exotoxins. Appropriate growth conditions can be customized for other prokaryotic hosts, as will be known to those of skill in the art, in light of the present disclosure.

Once the appropriate host has been constructed, and cultured under conditions appropriate for the production of HA, one will desire to separate the HA so produced. Typically, the HA will be secreted or otherwise shed by the recombinant organism into the surrounding media, allowing the ready isolation of HA from the media by known techniques. For example, HA can be separated from the cells and debris by filtering and in combination with separation from the media by precipitation by alcohols such as ethanol. Other precipitation agents include organic solvents such as acetone or quaternary organic ammonium salts such as cetyl pyridinium chloride (CPC).

A preferred technique for isolation of HA is described in U.S. Pat. No. 4,517,295, and which is incorporated herein by reference, in which the organic carboxylic acid, trichloroacetic acid, is added to the bacterial suspension at the end of the fermentation. The trichloroacetic acid causes the bacterial cells to clump and die and facilitates the ease of separating these cells and associated debris from HA, the desired product. The clarified supernatant is concentrated and dialyzed to remove low molecular weight contaminants including the organic acid. The aforementioned procedure utilizes filtration through filter cassettes containing 0.22 μm pore size filters. Diafiltration is continued until the conductivity of the solution decreases to approximately 0.5 megaohms.

The concentrated HA is precipitated by adding an excess of reagent grade ethanol or other organic solvent and the precipitated HA is then dried by washing with ethanol and vacuum dried, lyophilized to remove alcohol. The HA can then be redissolved in a borate buffer, pH 8, and precipitated with CPC or certain other organic ammonium salts such as CETAB, a mixed trimethyl ammonium bromide solution at 4 degree(s) Celsius. The precipitated HA is recovered by coarse filtration, resuspended in 1 M NaCl, diafiltered and concentrated as further described in the above referenced patent. The resultant HA is filter sterilized and ready to be converted to an appropriate salt, dry powder or sterile solution, depending on the desired end use.

A. Typical Genetic Engineering Methods which may be Employed

If cells without formidable cell membrane barriers are used as host cells, transfection is carried out by the calcium phosphate precipitation method, well known to those of skill in the art. However, other methods may also be used for introducing DNA into cells such as by nuclear injection, cationic lipids, electroporation, protoplast fusion or by the Biolistic(tm) Bioparticle delivery system developed by DuPont (1989). The advantage of using the DuPont system is a high transformation efficiency. If prokaryotic cells or cells which contain substantial cell wall constructions are used, the preferred method of transfection is calcium treatment using calcium chloride to induce competence or electroporation.

Construction of suitable vectors containing the desired coding and control sequences employ standard ligation techniques. Isolated plasmids or DNA fragments are cleaved, tailored, and religated in the form desired to construct the plasmids required. Cleavage is performed by treating with restriction enzyme (or enzymes) in suitable buffer. In general, about 1 μg plasmid or DNA fragments are used with about 1 unit of enzyme in about 20 μl of buffer solution. Appropriate buffers and substrate amounts for particular restriction enzymes are specified by the manufacturer. Incubation times of about 1 hour at 37° C. are workable.

After incubations, protein is removed by extraction with phenol and chloroform, and the nucleic acid is recovered from the aqueous fraction by precipitation with ethanol. If blunt ends are required, the preparation is treated for 15 minutes at 15° C. with 10 units of Polymerase I (Klenow), phenol-chloroform extracted, and ethanol precipitated. For ligation approximately equimolar amounts of the desired components, suitably end tailored to provide correct matching are treated with about 10 units T4 DNA ligase per 0.5 μg DNA. When cleaved vectors are used as components, it may be useful to prevent religation of the cleaved vector by pretreatment with bacterial alkaline phosphatase.

For analysis to confirm functional sequences in plasmids constructed, the first step was to amplify the plasmid DNA by cloning into specifically competent E. coli SURE cells (Stratagene) by doing transformation at 30–32° C. Second, the recombinant plasmid is used to transform E. coli K5 strain Bi833-741, which can produce the UDP-GlcA precursor, and successful transformants selected by antibiotic resistance as appropriate. Plasmids from the library of transformants are then screened for bacterial colonies that exhibit HA production. These colonies are picked, amplified and the plasmids purified and analyzed by restriction mapping. The plasmids showing indications of a functional HAS gene are then further characterized by any number of sequence analysis techniques which are known by those of ordinary skill in the art.

B. Source and Host Cell Cultures and Vectors

In general, prokaryotes were used for the initial cloning of DNA sequences and construction of the vectors useful in the invention. It is believed that a suitable source may be Gram-positive cells, particularly those derived from the Group C streptococcal strains. Bacteria with a single membrane, but a thick cell wall such as *Staphylococci* and *Stereptococci* are Gram-positive. Gram-negative bacteria such as *E. coli* contain two discrete membranes rather than one surrounding the cell. Gram-negative organisms tend to have thinner cell walls. The single membrane of the Gram-positive organisms is analogous to the inner plasma membrane of Gram-negative bacteria. The preferred host cells are *Streptococcus* strains that are mutated to become hyaluronidase negative or otherwise inhibited (EP144019, EP266578, EP244757). *Streptococcus* strains that have been particularly useful include *S. equisimilis* and *S. zooepidemicus*.

Prokaryotes may also be used for expression. For the expression of HA synthase in a form most likely to accommodate high molecular weight HA synthesis, one may desire to employ *Streptococcus* species such as *S. equisimilis* or *S. zooepidemicus*. The aforementioned strains, as well as *E. coli* W3110 (F-, lambda-, prototrophic, ATCC No. 273325), bacilli such as *Bacillus subtilis*, or other enterobacteriaceae such as *Serratia marcescens*, could be utilized to generate a "super" HAS containing host.

In general, plasmid vectors containing origins of replication and control sequences which are derived from species compatible with the host cell are used in connection with these hosts. The vector ordinarily carries an origin of replication, as well as marking sequences which are capable of providing phenotypic selection in transformed cells. For example, *E. coli* is typically transformed using pBR322, a plasmid derived from an *E. coli* species. pBR322 contains genes for ampicillin and tetracycline resistance and thus provides easy means for identifying transformed cells. A pBR plasmid or a pUC plasmid, or other microbial plasmid or phage must also contain, or be modified to contain, promoters which can be used by the microbial organism for expression of its own proteins.

Those promoters most commonly used in recombinant DNA construction include the lacZ promoter, tac promoter, the T7 bacteriophage promoter, and tryptophan (trp) promoter system. While these are the most commonly used, other microbial promoters have been discovered and utilized, and details concerning their nucleotide sequences have been published, enabling a skilled worker to ligate them functionally with plasmid vectors. Also for use with the present invention one may utilize integration vectors.

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in *Saccharomyces*, the plasmid YRp7, for example, is commonly used. This plasmid already contains the trp1 gene which provides a selection marker for a mutant strain of yeast lacking the ability to grow without tryptophan, for example, ATCC No. 44076 or PEP4-1. The presence of the trp1 lesion as a characteristic of the yeast host cell genome then provides an effective environment for detecting transformation by growth in the absence of tryptophan. Suitable promoting sequences in yeast vectors include the promoters for the galactose utilization genes, the 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, cytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture has become a routine procedure in recent years. Examples of such useful host cell lines are VERO and HeLa cells, Chinese hamster ovary (CHO) cell lines, and WI38, BHK, COS, and MDCK cell lines.

For use in mammalian cells, the control functions on the expression vectors are often provided by viral material. For example, commonly used promoters are derived from polyoma, Adenovirus 2, bovine papilloma virus and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

Further, it is also possible, and often desirable, to utilize promoter or control sequences normally associated with the desired gene sequence, provided such control sequences are compatible with the host cell systems. An origin of replication may be provided either by construction of the vector to include an exogenous origin, such as may be derived from SV40 or other viral (e.g., Polyoma, Adeno, BPV) source, or may be provided by the host cell chromosomal replication mechanism. If the vector is integrated into the host cell chromosome, the latter mechanism is often sufficient.

C. Isolation of a bona fide HA Synthase Gene from a Highly Encapsulated Strain of Group C *Streptococcus Equisimilis*.

Figure 8:
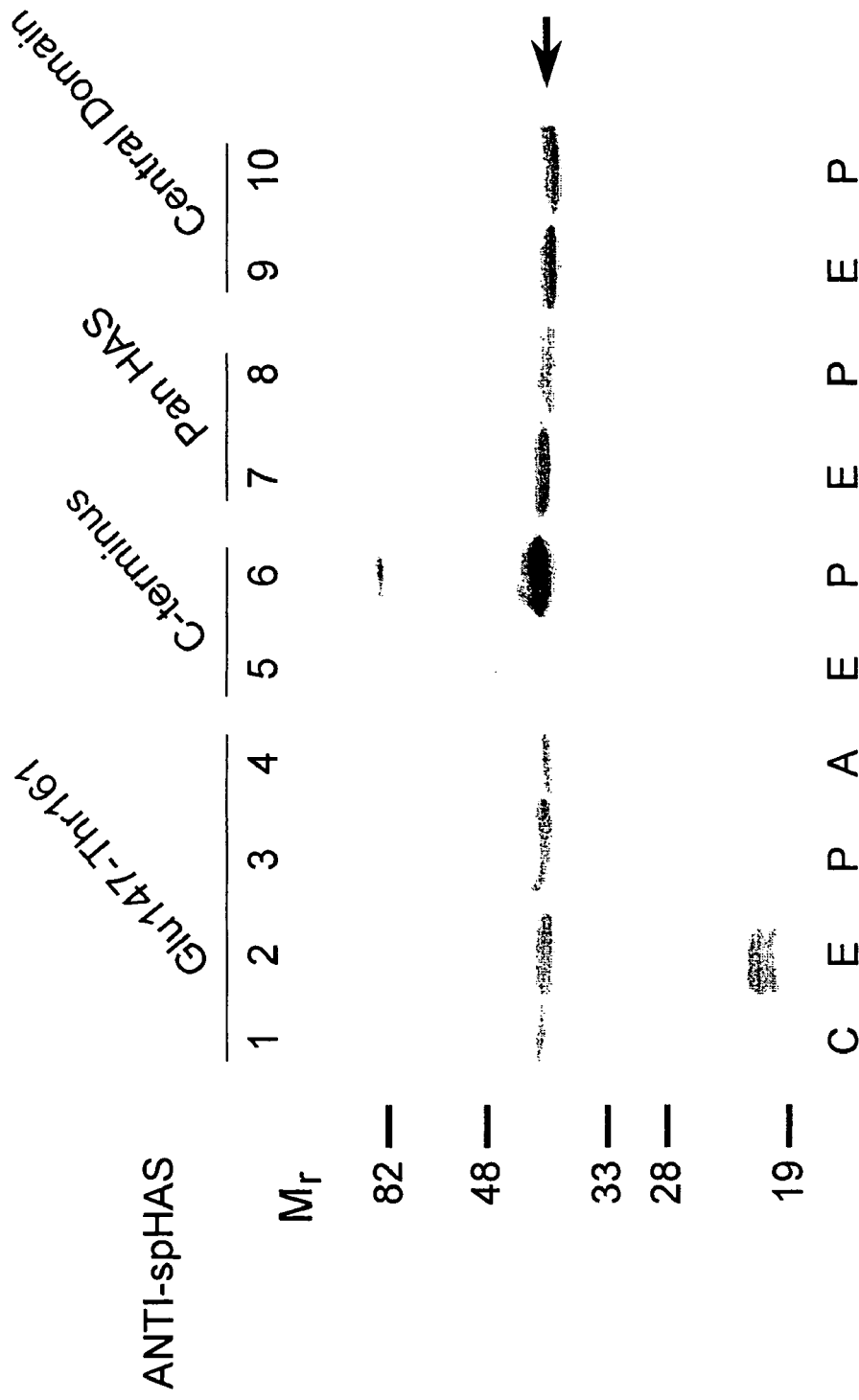
FIG. 8 is a Western blot analysis of recombinant seHAS using specific antibodies.

The encoded protein, designated seHAS, is 417 amino acids (calculated molecular weight of 47,778 and pI of 9.1) and is the smallest member of the HAS family identified thus far (FIG. 2). seHAS also migrates anomalously fast in SDS-PAGE ($M_r$~42 kDa) (FIGS. 5 and 8).

FIG. 8 is a graphical representation of a Western Blot analysis of recombinant seHAS using specific antibodies. Group C(C; lane 1) or Group A (A; lane 4) Streptococcal membranes and *E. coli* membranes (9 mgaane) containing recombinant seHAS (E; lanes 2, 7, and 9) or spHAS (P; lanes 3, 6, 8, and 10) were fractionated by reducing SDS-PAGE and electrotransferred to nitrocellulose. Strips of nitrocellulose were probed and developed as described in the application using purified IgG fractions raised to the following regions of spHAS: central domain peptide $E^{147}$-$T^{161}$ (lanes 1–4); C-terminus peptide (lanes 5–6); the complete protein (lanes 7 and 8); recombinant central domain (lanes 9 and 10). Nonimmune IgG or membranes from cells transformed with vector alone gave no staining as in lane 5.

The seHAS and spHAS protein (previously identified in U.S. Ser. No. 08/899,940) encoding sequences are 72% identical. The deduced protein sequence of seHAS was confirmed by reactivity with a synthetic peptide antibody (FIG. 8). Recombinant seHAS expressed in *E. coli* was recovered in membranes as a major protein (FIG. 5) and synthesized very large molecular weight HA in the presence of UDP-GlcNAc and UDP-Gla in vitro (FIG. 9).

Figure 9:
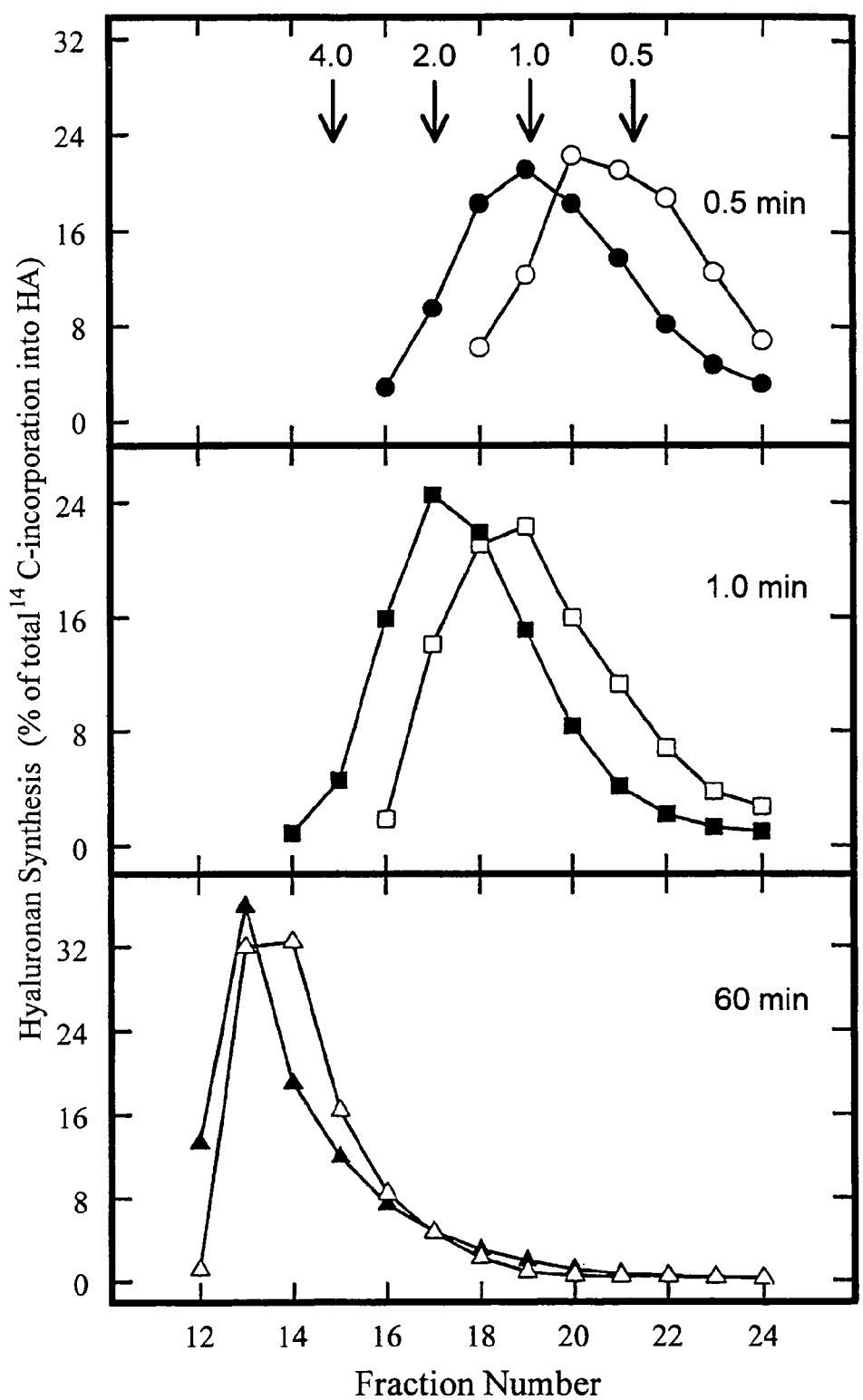
FIG. 9 is a kinetic analysis of the HA size distributions produced by recombinant seHAS and spHAS.

FIG. 9 shows a kinetic analysis of the HA size distributions produced by seHAS and spHAS. *E. coli* membranes containing equal amounts of seHAS or spHAS protein were incubated at 37° C. with 1.35 mM UDP-[$^{14}$C] GlcA ($1.3 \times 10^3$ dpm/nmol) and 3.0 mM UDP-GlcNAc as described in the application. These substrate concentrations are greater than 15 times the respective Km valves. Samples taken at 0.5, 1.0, and 60 min were treated with SDS and chromatographed over Sephacryl S400 HR. The HA profiles in the fractionation range of the column (fractions 12–24) are normalized to the percent of total HA in each fraction. The values above the arrows in the top panel are the MWs (in millions) of HA determined directly in a separate experiment using a Dawn multiangle laser light scattering instrument (Wyatt Technology Corp.). The size distributions of HA synthesized by seHAS (●,■,▲) and spHAS (○,□,_) at 0.5 min (○,●), 1.0 min (□,■) and 60 min (_,▲) are shown as indicated. Analysis showed that seHAS and spHAS are essentially identical in the size distribution of HA chains they synthesize (FIG. 9). SeHAS is twice as fast as spHAS in its ability to make HA.

C.1 Bacterial Strains and Vectors

The mucoid group C strain D181; (*Streptococcus equisimilis*) was obtained from the Rockfeller University Collection. The *E. coli* host strains Sure and XL1-Blue MRF' were from Stratagene and strain Top10 F' was from Invitrogen. Unless otherwise noted, Stereptococci were grown in THY and *E. coli* strains were grown in LB medium. pKK-223 Expression vector was from Pharmacia, PCR 2.1 cloning vector was from Invitrogen, and predigested λ Zap Express TM Bam HI/CIAP Vector was from Stratagene.

C.2 Recombinant DNA and Cloning

High molecular mass Genomic DNA from *Streptococcus equisimilis* isolated by the method of Caparon and Scott (as known by those with ordinary skill in the art) was partially digested with Sau3A1 to an average size of 2–12 kb. The digested DNA was precipitated with ethanol, washed and ligated to the Bam HI/CIAPλ Zap Express vector. Ligated DNA was packaged into phage with a Packagene™ extract obtained from Promega. The titer of the packaged phage library was checked using XL1-Blue MRF' *E. coli* as a host.

C.3 Degenerate PCR Amplification

Degenerate oligonucleotides were designed based upon conserved sequences among spHAS (*Streptococcus pyogenes*), DG42 (*Xenopus laevis* HAS; 19) and nodC (a *Rhizobium meliloti* nodulation factor; 20) and were used for PCR amplification with D181 genomic DNA as a template. Amplification conditions were 34 cycles at: 94° C. for 1 min, 44° C. for 1 min, 72° C. for 1.5 min followed by a final extension at 72° C. for 10 min. Oligonucleotide HADRF1. 5'-GAY MGA YRT YTX ACX MT TAY GCT ATH GAY TTR GG-3' (sense strand) corresponds to the sequence $D^{259}$RCLTNYAIDL (spHAS). Oligonucleotide HACTR1, 5'-ACG WGT WCC CCA NTC XGY ATT TTT NAD XGT RCA-3' (antisense strand) corresponds to the region $C^{404}$TIKNTEWGTR (spHAS). The degeneracy of bases at some positions are represented by nomenclature adopted by the IUPAC in its codes for degenerate bases listed in Table IV.

TABLE IV

IUPAC Codes - Degenerate Bases
The International Union for Pure and Applied Chemistry (IUPAC) has established a standard single-letter designation for degenerate bases. These are:

B = C + G + T
D = A + G + T
H = A + C + T
K = T + G
M = A + C
N = A + C + G + T
R = A + G
S = G + C
W = A + T
V = A + C + G
X = a minor bases (specified elsewhere)
Y = C + T These two oligonucleotides gave a 459 bp PCR product, which was separated on an agarose gel and purified using the BIO-101 Geneclean kit. This fragment was then cloned into PCR2.1 vector using TOP 10 F' cells as a host according to the manufacturer's directions. Double stranded plasmid DNA was purified from *E. coli* (Top 10 F') using the QIAfilter Plasmid Midi Kit (Qiagen). Two other degenerate sense primers were also synthesized: HAVAF1,5'-GTN GCT GCT GTW RTX CCW WSX TWT MY GAR GA-3' (corresponding to the region $V^{66}$AAVIPSYNE of spHAS) and HAVDF1, 5'-GTX RWT GAY GGN WSX WSN RAX GAT GAX GC-3' (based on $V^{100}$DDGSSNTD of spHAS). Two unique antisense primers were synthesized based on the sequence of the 459 bp PCR product. These were: D181.2, 5'-GAA GGA CTT GTT CCA GCG GT-3' and D181.4, 5'-TGA ATG TTC CGA CAC AGG GC-3'. Each of the two degenerate sense primers, when used with either D181.2 or D181.4 to amplify D181 genomic DNA, gave expected size PCR products. The four PCR products were cloned and sequenced using the same strategy as above. For each PCR product, sequences obtained from six different clones were compared in order to derive a consensus sequence. Thus we obtained a 1042 bp sequence with a continuous ORF with high homology to spHAS.

C.4 Library Screening

Two molecular probes were used to screen the library; the cloned 459 bp PCR product and oligonucleotide D181.5 (5'-GCTTGATAGGTCACCAGTGTCACG-3'; derived from the 1042 bp sequence). The 459 bp PCR product was radiolabeled using the Prime-It 11 random primer labeling Kit (Stratagene) according to the manufacturers instructions. Oligonucleotides were labeled by Kinace-It Kinasing Kit (Stratagene) using [y$^{32}$P]ATP. Radiolabeled products were separated from nonlabeled material on NucTrap Push columns (Stratagene). The oligoprobe hybridized specifically with a D181 genomic digest on Southern blots. To screen the λ phage library, XLBLUE MRF' was used as a host (3000 plaques/plate) on Nitrocellulose membranes containing adsorbed phage, were prehybridized at 60° C. and hybridized with 5'-end labeled oligonucleotide, D181.5, in QuikHyb Hybridization solution (Stratagene) at 80° C. according to instructions.

The membranes were then washed with 2×SSC buffer and 0.1% (w/v) SDS at room temperature for 15 min, at 60° C. with 0.1×SSC buffer and 0.1% SDS (w/v) for 30 min, dried and then exposed to Bio-Max MS film overnight at −70° C. Positive plaques were replated and rescreened twice. Pure positive phages were saved in SM buffer with chloroform. PCR on these phages with vector primers revealed 3 different insert sizes.

PCR with a combination of vector primers and primers from different regions of the cloned 1042 bp sequence revealed that only one of the three different phages had the complete HAS gene. The insert size in this phage was 6.5 kb. Attempts to subclone the insert into plasmid form by autoexcision from the selected phage library clone failed. Therefore, a PCR strategy was applied again on the pure positive phage DNA to obtain the 5' and 3' end of the ORF. Oligonucleotide primers D181.3 (5'-GCCCTGTGTCGGAACATTCA-3') and T3 (vector primer) amplified a 3 kb product and oligonucleotides D181.5 and T7 (vector primer) amplified a 2.5 kb product. The 5' and 3'-end sequences of the ORF were obtained by sequencing these two above products. Analysis of all PCR product sequences allowed us to reconstruct the ORF of the 1254 bp seHAS gene.

C.5 Expression Cloning of the seHAS

Primers were designed at the start and stop codon regions of seHAS to contain an EcoR1 restriction site in the sense oligonucleotide (5'-AGGATCCGAATTCATGAGAACATTAAAAAACCTC-3') and a Pst1 site in the antisense oligonucleotide (5'-AGAATTCTGCAGTTATAATAATTTTTTACGTGT-3'). These primers amplified a 1.2 kb PCR product from D181 genomic DNA as well as from pure hybridization-positive phage. The 1.2 kb product was purified by agarose gel electrophoresis, digested with Pst1 and EcoR1 and cloned directionally into Pst1- and EcoR1-digested pKK223 vector. The ligated vector was transformed into E. coli SURE cells that were then grown at 30° C. This step was practically important since other host cells or higher temperatures resulted in deletions of the cloned insert. Colonies were isolated and their pDNA purified. Out of six colonies (named a,b,c,d,e, and f), five had the correct size insert, while one had no insert.

C.6 HA Synthase Activity

HA synthase activity was assayed in membranes prepared from the 5 above clones. Fresh log phase cells were harvested at 3000 g, washed at 4° C. with PBS and membranes were isolated by a modification of a protoplast method as known by those of ordinary skill in the art. Membrane preparations from Streptococcus pyogenes and Streptococcus equisimilis were also obtained by modification of a different protoplast procedure. Membranes were incubated at 37° C. in 50 mM sodium and potassium phosphate, pH 7.0 with 20 mM MgCl$_2$, 1 mM DTE, 120 μM UDP-GlcA and 300 μM UDP-GlcNAc. Incorporation of sugar was monitored by using UDP-[$^{14}$C]GlcA (318 mCi/mmol; ICN) and/or UDP-[$^3$H]GlcNAc (29.2 Ci/mmol NEN). Reactions were terminated by addition of SDS to a final concentration of 2% (w/v). Product HA was separated from precursors by descending paper chromatography and measured by determining incorporated radioactivity at the origin.

C.7 Gel Filtration Analysis

Radiolabeled HA produced in vitro by membranes containing recombinant seHAS or spHAS was analyzed by chromatography on a column (0.9×40 cm) of Sephacryl S500 HR (Pharmacia Biotech Inc.). Samples (0.4 ml in 200 mM NaCl, 5 mM Tris-HCl, pH 8.0, plus 0.5% SDS) were eluted with 200 mM, NaCl, 5 mM Tris-HCL, and pH 8.0 and 0.5 ml fractions were assessed for $^{14}$C and/or $^3$H radioactivity. Authenticity of the HA polysaccharide was assessed by treatment of a separate identical sample with the HA-specific hyaluronate lyase of Streptomyces hyalurolyticus (EC 4.2.2.1) at 37° C. for 3 hrs. The digest was then subjected to gel filtration.

C.8 SDS-PAGE and Western Blotting

SDS-PAGE was performed according to the Laemmli method. Electrotransfers to nitrocellulose were performed within standard blotting buffer with 20% methanol using a Bio-Rad mini Transblot device. The blots were blocked with 2% BSA in TBS. Protein A/G alkaline phosphatase conjugate (Pierce) and p-nitroblue tetrazolium/5-bromo-4-chloro-3 indolyl phosphate p-toluidine salt were used for detection.

C.9 DNA Sequence and Analysis

Plasmids were sequenced on both strands using fluorescent labeled vector primers. Sequencing reactions were performed using a Thermosequenase™ kit for fluorescent labeled primers (with 7-deazaG). Samples were electrophoresed on a Pharmacia ALF Express DNA Sequencer and data were analyzed by the ALF Manager Software v3.02. Internal regions of inserts were sequenced with internal primers using the ABI Prism 377 (Software version 2.1.1). Ambiguous regions were sequenced manually using Sequenase™ 7-deaza—DNA polymerase, 7-deaza GTP master mix (USB) and [α-$^{35}$S] dATP (Amersham Life Sciences). The sequences obtained were compiled and analyzed using DNASIS, v2.1 (Hitachi Software Engineering Co., Ltd.). The nucleotide and amino acid sequences were compared with other sequences in the Genbank and other databases.

C.10 Identification of seHAS

Identification of seHAS was accomplished by utilizing a PCR approach with oligonucleotide primers based on several regions of high identity among spHAS, DG42 (now known to be a developmentally regulated X. laevis HAS and designated xlHAS) and NodC (a Rhizobium β-GlcNAc transferase). The xlHAS and NodC proteins are, respectively, ~50% and ~10% identical to spHAS. This strategy yielded a 459 bp PCR product whose sequence was 66.4% identical to spHAS, indicating that a Group C homologue (seHAS) of the Group A (spHAS) HA synthase gene had been identified. The complete coding region of the gene was then reconstructed using a similar PCR-based strategy. A final set of PCR primers was then used to amplify the complete ORF from genomic DNA. When this 1.2 kb PCR fragment was incorporated into the expression vector pKK223 and transformed into *E. coli* SURE cells, HA synthetic activity was demonstrated in isolated membranes from 5 of the 5 colonies tested.

The ORF of the reconstructed gene encodes a novel predicted protein of 417 amino acids that was not in the database and it is two amino acids shorter than spHAS. The two bacterial proteins are 72% identical and the nucleic acid sequences are 70% identical. The predicted molecular weight of the seHAS protein is 47,778 and the predicted isoelectric point is at pH 9.1. Three recently identified mammalian HASs (muHAS1, muHAS2, muHAS3, FIG. 2) are similar to the bacterial proteins. The overall identity between the two groups is ~28–31%, and in addition many amino acids in seHAS are highly conserved with those of the eukaryotic HASs (e.g. K/R or D/E substitutions). A98R, the PBCY-1 HAS is 28–33 percent identical to the mammalian HASs, and is predicted to have a similar topology in the lipid membrane. Within mammalian species the same family members are almost completely identical (e.g. muHAS1 and huHAS1 are 95% identical; muHAS2 and huHAS2 are 98% identical). However, and as shown in FIG. 3, even within the same species the different HAS family members are more divergent (e.g. muHAS1 and muHAS2 are 53% identical; muHAS1 and muHAS3 are 57% identical; muHAS2 and muHAS3 are 71% identical).

Figure 10:
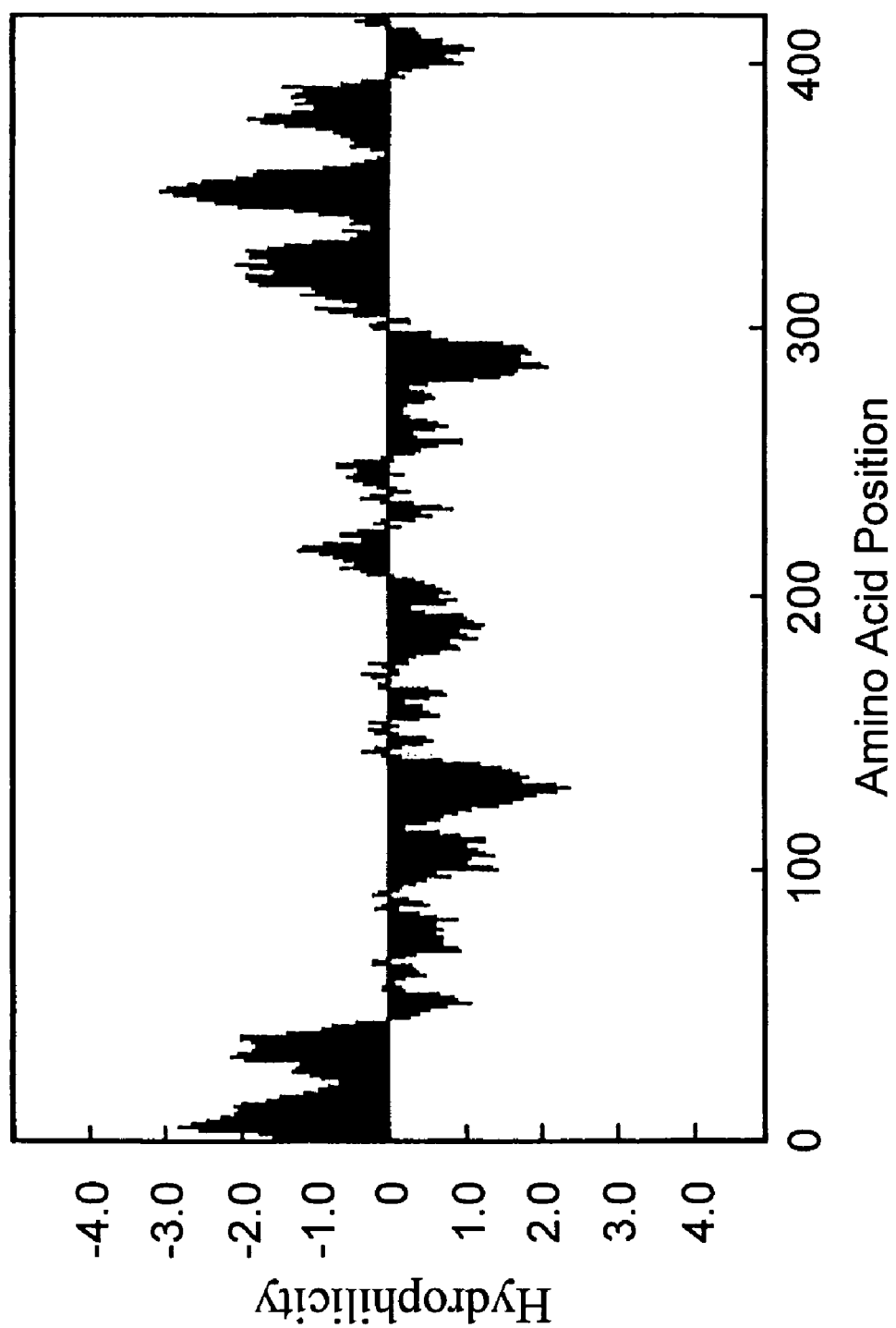
FIG. 10 graphically depicts the hydropathy plots for seHAS and predicted membrane associated regions.

FIG. 10 shows hydropathy plots for seHAS and predicted membrane topology. The hydrophilicity plot for the streptococcal Group C HAS was generated by the method of Kyte and Doolittle (J. Mol. Biol. 157, 105, 1982) using DNASIS. The protein is predicted to be an integral membrane protein.

Figure 11:
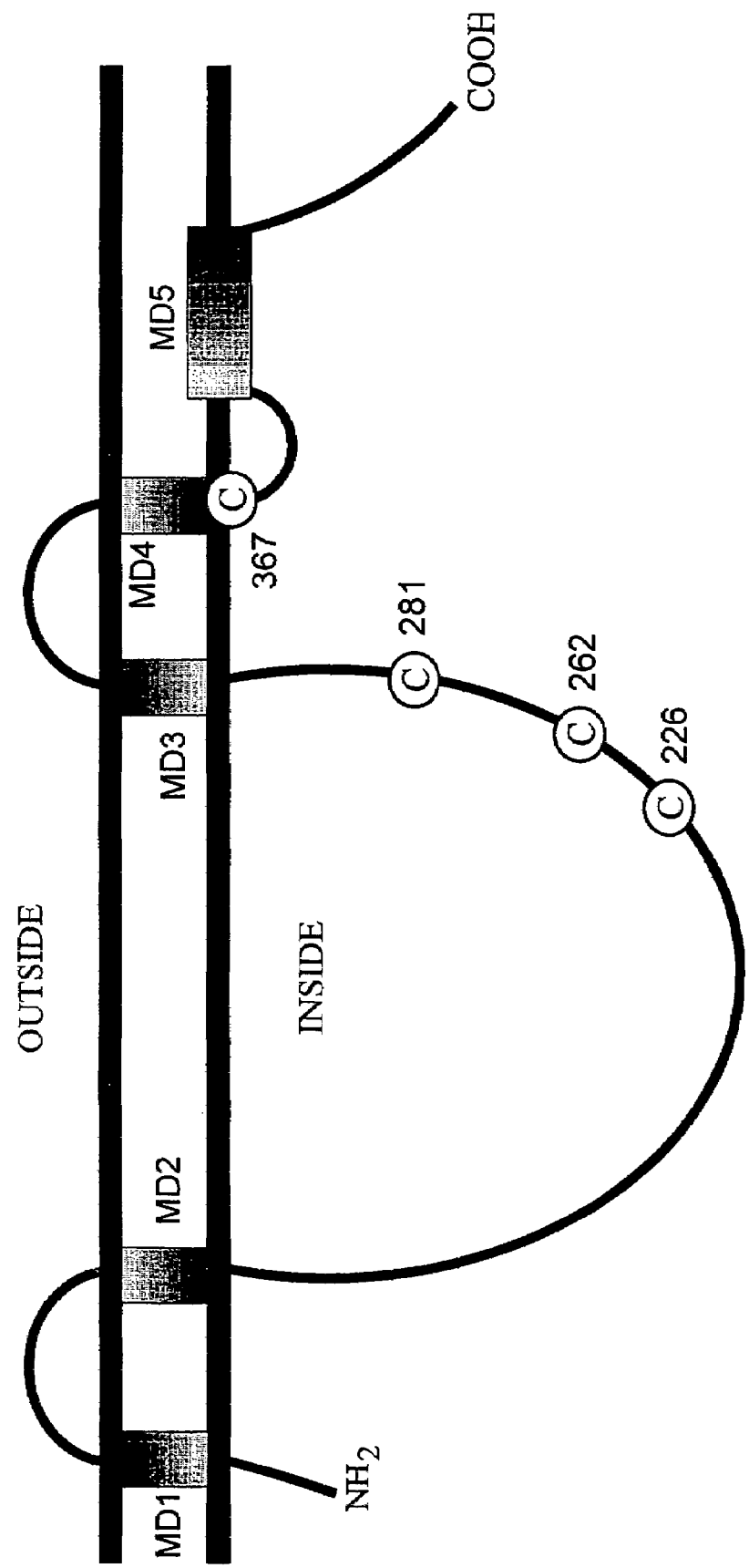
FIG. 11 is a graphical model for the topologic organization of seHAS in the membrane.

FIG. 11 shows a model for the topologic organization of seHAS in the membrane. The proposed topology for the protein conforms to the charge-in rule and puts the large central domain inside. This domain is likely to contain most of the substrate binding and catalytic functions of the enzyme. $Cys^{226}$ in seHAS, which is conserved in all HAS family members, as well as the other three cysteines are shown in the central domain. $Cys^{281}$ is a critical residue whose alteration can dramatically alter the size distribution of HA product synthesized by the enzyme.

The overall membrane topology predicted for seHAS is identical to that for spHAS and the eukaryotic HASs reported thus far. The protein has two putative transmembrane domains at the amino terminus and 2–3 membrane-associated or transmembrane domains at the carboxyl end. The hydropathy plots for the two streptococcal enzymes are virtually identical and illustrate the difficulty in predicting the topology of the extremely hydrophobic region of ~90 residues at $K^{313}$–$R^{406}$ in seHAS ($K^{313}$–$K^{405}$ in spHAS).

seHAS was efficiently expressed in *E. coli* cells. Roughly 10% of the total membrane protein was seHAS as assessed by staining of SDS-PAGE gels (FIG. 5). The prominent seHAS band at 42 kD is quantitatively missing in the vector-only control lane. This unusually high level of expression for a membrane protein is also found for spHAS, using the same vector in SURE cells. About 8% of the membrane protein is spHAS in *E. coli* SURE cells. In contrast, the amount of seHAS in Group C membranes is not more than 1% of the total membrane protein. The spHAS in Group A membranes is barely detectable. The recombinant seHAS expressed in *E. coli* SURE cells does not synthesize HA in vivo, since these cells lack UDP-GlcA, one of the required substrates. Membranes, however containing the recombinant seHAS protein synthesize HA when provided with the substrates UDP-GlcNAc and UDP-GlcA (FIG. 12).

Figure 12:
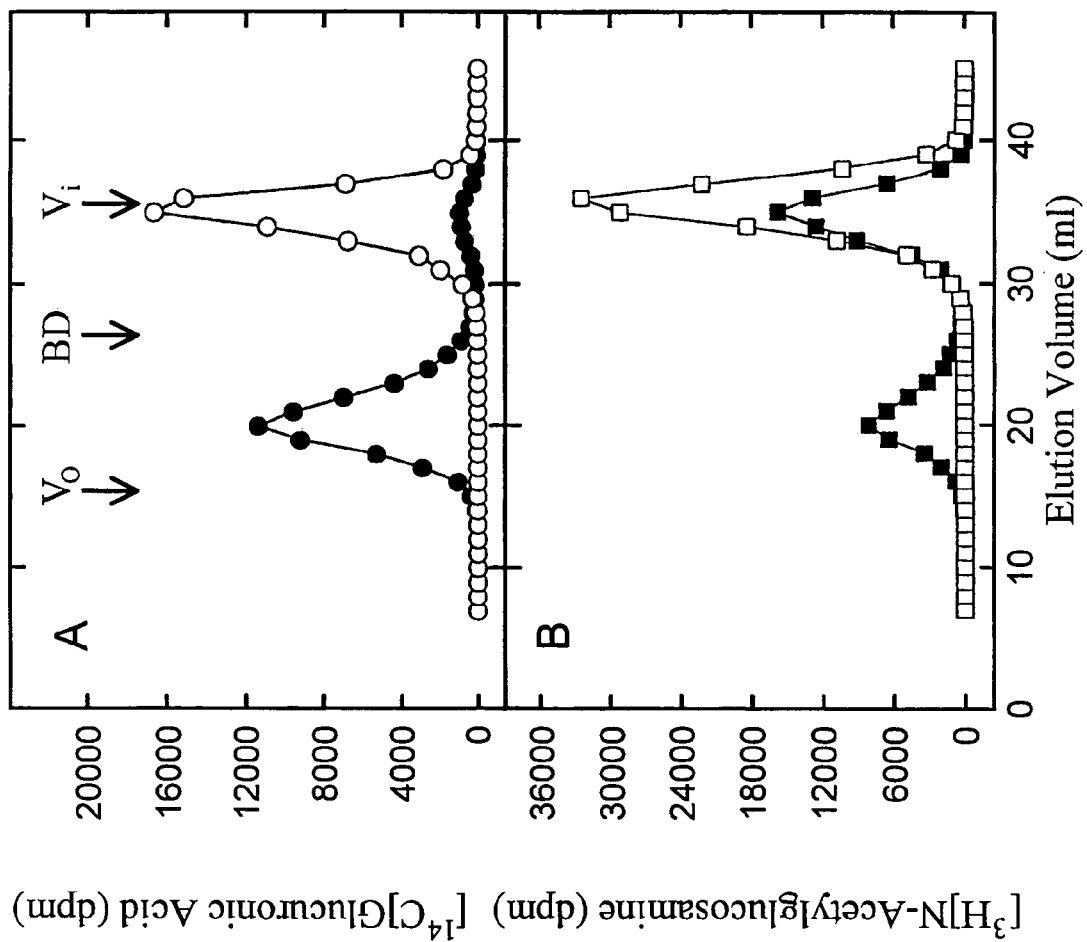
FIG. 12 is a demonstration of the synthesis of authentic HA by the recombinant seHAS.

FIG. 12 shows the synthesis of authentic HA by recombinant seHAS. *E. coli* membranes (69 µg) prepare from cells containing recombinant seHAS or vector alone were incubated at 37° C. for 1 hour with 700 µM UDP-[$^3$H]GlcNAc ($2.78 \times 10^3$ dpm/nmol; □,■) and 300 µM UDP-[$^{14}$C]GlcA ($3.83 \times 10^3$ dpm/nmol; ○,●) in a final volume of 200 µl as described herein. The enzyme reaction was stopped by addition of EDTA to a final concentration of 25 mM. Half the reaction mix was treated with *Streptomyces* hyaluronidase at 37° C. for 3 hours. SDS (2%, w/v) was added to hyaluronidase-treated (○,□) and untreated (●,■) samples, which were heated at 90° C. for 1 min. The samples were diluted to 500 µl with column buffer (5 mM Tris, 0.2 M Nacl, pH 8.0), clarified by centrifugation and 200 µl was injected onto a Sephacryl S-500 HR column. Fractions (1 ml) were collected and radioactivity was determined. BD is the peak elution position position of blue dextran (~$2 \times 10^6$ DA; Pharmacia). $V_o$ marks the excluded volume and $V_i$ the included volume. The ratio of [$^{14}$c] GlcA: [$^3$H] GlcNAc incorporated into the total amount of HA fractionated on the column is 1.4, which is identical to the ratio of specific activities of the two substrates. Therefore, the molar ratios of the sugars incorporated into product is 1:1 as predicted for authentic HA. Membranes from cells transformed with vector alone did not synthesize HA.

Using 120 µM UDP-GlcA and 300 µM UDP-GlcNAc, HA synthesis was linear with membrane protein (at $\leq$0.2 µg) and for at least 1 hour. Also, membranes prepared from nontransformed cells or cells transformed with vector alone have no detectable HAS activity. HA synthesis is negligible if $Mg^{+2}$ is chelated with EDTA (<5% of control) or if either of the two substrates are omitted (~2% of control). Recombinant seHAS also showed the expected specificity for sugar nucleotide substrates, being unable to copolymerize either UDP-GalA, UDP-Glc or UDP-GalNAc with either of the two normal substrates (Table II).

Based on gel filtration analysis, the average mass of the HA synthesized by seHAS in isolated membranes is 5–10× $10^6$ Da. The product of the recombinant seHAS is judged to be authentic HA based on the equimolar incorporation of both sugars and its sensitivity to degradation by the specific *Streptomyces* hyaluronidase (FIG. 12). Although the conditions for total HA synthesis were not optimal (since ~90% of one substrate was incorporated into product), the enzyme produced a broad distribution of HA chain lengths. The peak fraction corresponds to an HA mass of $7.5 \times 10^6$ Da which is a polymer containing approximately 36,000 monomeric sugars. The distribution of HA sizes resolved on this column ranged from 2–$20 \times 10^6$ Da.

The deduced protein sequence of seHAS was confirmed by the ability of antibodies to the spHAS protein to cross-react with the Group C protein (FIG. 8). Polyclonal antibodies to the whole spHAS protein or to just the central domain of spHAS also reacted with the seHAS protein. Antipeptide antibody to the C-terminus of spHAS did not cross-react with this somewhat divergent region in the seHAS protein. However, antipeptide antibody directed against the spHAS sequence $E^{147}$-$T^{161}$ recognized the same predicted sequence in seHAS. The antipeptide antibody also reacts with the native seHAS and spHAS proteins in streptococcal membranes and confirms that the native and recombinant enzymes from both species are of identical size. Like the spHAS protein, seHAS migrates anomalously fast on SDS-PAGE. Although the calculated mass is 47,778 Da, the Mr by SDS-PAGE is consistently ~42 kDa.

Because of the sequence identity within their central domain regions and the overall identical structure predicted for the two bacterial enzymes, the peptide-specific antibody against the region $E^{147}$-$T^{161}$ can be used to normalize for HAS protein expression in membranes prepared from cells transformed with genes for the two different enzymes. Using this approach, membranes with essentially identical amounts of recombinant spHAS or seHAS were compared with respect to the initial rate of HA synthesis and the distribution of HA product size.

As shown for spHAS, the synthesis of HA chains by seHAS is processive. The enzymes appear to stay associated with a growing HA chain until it is released as a final product. Therefore, it is possible to compare the rates of HA elongation by seHAS and spHAS by monitoring the size distribution of HA chains produced at early times, during the first round of HA chain synthesis. Based on gel filtration analysis of HA product sizes at various times, we estimated that the average rate elongation by seHAS is about 9,000 monosaccharides/minute at 37° C. (FIG. 9). In five minutes, the enzymes can polymerize an HA chain of $5-10 \times 10^6$ Da. During a 60 min incubation, therefore, each enzyme molecule could potentially initiate, complete and release on the order of 5–8 such large HA molecules. At early times (e.g. $\leq 1$ min), reflecting elongation of the first HA chains, the size distribution of HA produced by seHAS was shifted to larger species compared to spHAS. By 60 min the two distributions of HA product sizes are indistinguishable.

The cloned seHAS represents the authentic Group C HA synthase. Previously reported or disclosed "Group C" proteins are, therefore, not the true Group C HAS. The seHAS protein is homologous to nine of the currently known HA synthases from bacteria, vertebrates, and a virus that now comprise this rapidly growing HA synthase family. This homology is shown particularly in FIG. 2. In mammals three genes, designated HAS 1, HAS 2 and HAS 3, have been identified and mapped to three different chromosomes in both human and mouse. In amphibians the only HAS protein identified thus far is the developmentally regulated DG42, which was cloned in 1988 and recently shown to encode the HA synthase activity by analysis of the recombinant protein in yeast membranes. Probably other *X. laevus* HAS genes will soon be identified.

A divergent evolution model suggests that a primitive bacterial HAS precursor may have been usurped early during vertebrate development or the bacterial pathogenic strategy of making an HA capsule was developed when a primitive bacteria captured in primordial HAS. Convergent evolution of the bacterial and eukaryotic HAS enzymes to a common structural solution seems unlikely, but may have occurred.

None of the three mammalian isozymes for HAS have yet been characterized enzymatically with respect to their HA product size. At least ten identified HAS proteins are predicted to be membrane proteins with a similar topology. HA synthesis occurs at the plasma membrane and the HA is either shed into the medium or remains cell associated to form the bacterial capsule or a eukaryotic pericellular coat. The sugar nucleotide substrates in the cytoplasm are utilized to assemble HA chains that are extruded through the membrane to the external space.

The protein topology in the very hydrophobic carboxyl portion of the HAS protein appears to be critical in understanding how the enzymes extend the growing HA chain as it is simultaneously extruded through the membrane. For example, the unprecedented enzymatic activity may require unusual and complex interactions of the protein with the lipid bilayer. Preliminary results based on analysis of spHAS-alkaline phosphatase fusion proteins indicate that the amino and carboxyl termini and the large central domains are all intracellular, as shown in FIGS. 10 and 11.

The seHAS protein also contains a large central domain (~63% of the total protein) that appears to contain the two substrate binding sites and the two glycosyltransferase activities needed for HA synthesis. Although current software programs cannot reliably predict the number or nature of membrane-associated domains within the long C-terminal hydrophobic stretch, the proposed topological arrangement agrees with the present evidence and applies as well to the eukaryotic enzymes, which are ~40% larger primarily due to extention of the C-terminal end of the protein with 2 additional predicted transmembrane domains.

Four of the six Cys residues in spHAS are conserved with seHAs. Only Cys225 in both bacterial enzymes is conserved in all members of the HAS family. Since sulfhydryl reactive agents, such as p-mercurobenzoate or NEM, greatly inhibit HAS activity, it is likely that this conserved Cys is necessary or important for enzyme activity. Initial results from site-directed mutagenesis studies, however, indicate that a C225S mutant of spHAS is not inactive, it retains 5–10% of wildtype activity.

Figure 13:
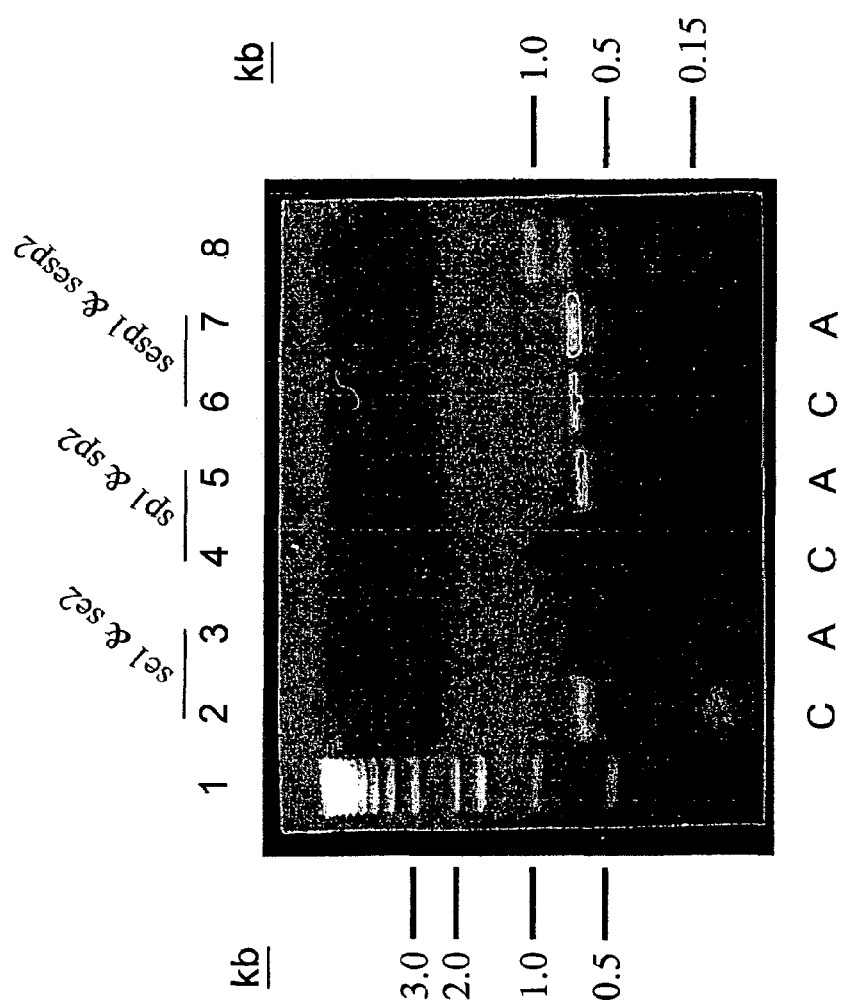
FIG. 13 depicts the recognition of nucleic acid sequences encoding seHAS, encoding spHAS, or encoding both seHAS and spHAS using specific oligonucleotides and PCR.

The recognition of nucleic acid sequences encoding only seHAS, only spHAS, or both seHAS and spHAS using specific oligonucleotides is shown in FIG. 13. Three pairs of sense-antisense oligonucleotides were designed based on the sequence of ID SEQ NO. 1 and the coding sequence for spHAS. The seHAS based nucleic acid segments (se1-se2 and sesp1-sesp2) are listed in SEQ. ID NOS: 3, 4, 5, and 6. These three oligonucleotide pairs were hybridized under typical PCR reactions with genomic DNA from either Group C (seHAS) (lanes 2, 4, and 6) or Group A (spHAS) (lanes 3,5, and 7) streptococci. Lanes 1 and 8 indicate the positions of MW standards in kb (kilobases). The PCR reactions were performed using Taq DNA polymerase (from Promega) for 25 cycles as follows: 94 degrees Celsius for 1 minute to achieve DNA denaturation, 48 degrees Celsius (42 degrees Celsius for the smaller common sesp primers) for 1 minute to allow hybridization, and 72 degrees Celsius for 1.5 minutes for DNA synthesis. The PCR reaction mixtures were then separated by electrophoresis on a 1% agarose gel.

The se1-se2 primer pair was designed to be uniquely specific for the Group C HAS (seHAS). The sp1-sp2 primer pair was designed to be uniquely specific for the Group A HAS (spHAS). The sesp1-sesp2 primer pair was designed to hybridize to both the Group A and Group C HAS nucleic acid sequences. All three primer pairs behaved as expected, showing the appropriate ability to cross-hybridize and support the generation of PCR products that were specific and/or unique.

The oligonucleotides used for specific PCR or hybridization are listed in SEQ. ID NOS: 3, 4, 5, and 6. The synthetic oligonucleotides of SEQ ID NOS: 3, 4, 5, and 6 are indicated in the corresponding regions of SEQ ID NO. 1. These regions are in bold face and marked, respectively as primers se1, se2, sesp1, and sesp2. The #1 indicates primers in the sense direction, while the #2 indicates a primer in the antisense direction. Each of the four oligonucleotides will hybridize specifically with the seHAS sequence and the appropriate pairs of sense/antisense primers are suitable for use in the polymerase chain reaction as shown in FIG. 13.

FIG. 7 shows a gel filtration analysis of hyaluronic acid synthesized by recombinant HAS expressed in yeast membranes. A DNA fragment encoding the open reading frame of 419 amino acid residues corresponding to spHAS (with the original Val codon switched to Met) was subcloned by standard methods in the pYES2 yeast expression vector (from Invitrogen) to produce pYES/HA. Membranes from cells with this construct were prepared by agitation with glass beads. The samples derived from pYES/HA constructs contained substantial HA synthase activity and the "42 kDa" HAS protein was detected by Western analysis using specific antibodies; membranes from cells with vector alone possessed neither activity nor the immunoreactive band (not shown). Membranes (315 ug protein) were first incubated with carrier free UDP-[$^{14}$C]GlcA (1 uCi$^{14}$C) amd 900 uM unlabeled UDP-GlcNAc in 50 mM Tris, pH 7, 20 mM MgCl2, 1 mM DTT, and 0.05 M NaCl (450 ul reaction volume) at 30 degrees Celsius for 1.5 minutes. After this pulse-label period nonradiolabeled UDP-GlcA was then added to final concentrations of 900 uM. Samples (100 uL) were taken after the pulse at 1.5 min (dark circle), and 15 (black square), and 45 (black triangle) min after the "chase." The reactions were terminated by the addition of SDS to 2% and heating at 95 degrees Celsius for 1 min. The samples were clarified by centrifugation (10,000×g, 5 min) before injection of half of the sample onto a Sephacryl S-500HR gel filtration column (Pharmacia; 1×50 cm) equilibrated in 0.2 M NaCl, 5 mM Tris, pH 8.

The column was eluted at 0.5 ml/min and radioactivity in the fractions (1 ml) was quantitated by liquid scintillation counting after adding BioSafe11 cocktail (4.5 ml, Research Products Intl.). The void volume and the totally included volumes were at elution volumes of 14 ml and 35.5 ml, respectively. The peak of blue dextran (average 2×10 6 Da) eluted at 25–27 ml. The recombinant HAS expressed in the eukaryotic yeast cells makes high molecular weight hyaluronic acid in vitro.

Thus it should be apparent that there has been provided in accordance with the present invention a purified nucleic acid segment having a coding region encoding enzymatically active HAS, methods of producing hyaluronic acid from the seHAS gene, and the use of hyaluronic acid produced from a HAS encoded by the seHAS gene, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

What is claimed:

1. A recombinant host cell comprising at least one expression construct comprising a hyaluronan synthase gene, wherein the hyaluronan synthase gene encodes a single protein that is a dual-action catalyst that utilizes UDP-GlcA and UDP-GlcNAc to synthesize HA.

2. The recombinant host cell of claim 1, wherein the recombinant host cell produces HA.

3. The recombinant host cell of claim 1, wherein the at least one expression construct further comprises at least one gene encoding an enzyme for synthesis of a hyaluronic acid sugar precursor.

4. The recombinant host cell of claim 3, wherein the at least one gene encoding an enzyme for synthesis of a hyaluronic acid sugar precursor is selected from the group consisting of a pyrophosphorylase, a transferase, a mutase, a dehydrogenase, or an epimerase, capable of producing UDP-GlcNAc or UDP-GlcUA.

5. The recombinant host cell of claim 1, further comprising a second at least one expression construct having at least one gene encoding an enzyme for synthesis of a hyaluronic acid sugar precursor.

6. The recombinant host cell of claim 1, wherein the recombinant host cell further comprises at least one integrated or plasmid-borne gene encoding an enzyme for synthesis of a hyaluronic acid sugar precursor.

7. The recombinant host cell of claim 1, wherein hyaluronic acid sugar precursors are expressed in the recombinant host cell by endogenous genes thereof.

8. The recombinant host cell of claim 1, wherein the hyaluronan synthase gene is isolated from a streptococcal source.

9. The recombinant host cell of claim 1, wherein the hyaluronan synthase gene is isolated from a microorganism.

10. The recombinant host cell of claim 1, wherein the hyaluronan synthase protein comprises a central intracellular domain, at least two transmembrane domains at an amino end thereof, and at least two membrane-associated domains at a carboxyl end thereof.

11. The recombinant host cell of claim 1, wherein the at least one expression construct further comprises a promoter operatively linked to the hyaluronan synthase gene.

12. A recombinant host cell comprising:
  at least one expression construct comprising a hyaluronan synthase gene, wherein the hyaluronan synthase gene encodes a single protein that is a dual-action catalyst that utilizes UDP-GlcA and UDP-GlcNAc to synthesize HA;
  at least one expression construct having at least one gene encoding an enzyme for synthesis of a hyaluronic acid sugar precursor; and
  wherein the recombinant host cell produces HA.

13. The recombinant host cell of claim 12, wherein the hyaluronan synthase gene is isolated from a streptococcal source.

14. The recombinant host cell of claim 12, wherein the hyaluronan synthase gene is isolated from a microorganism.

15. The recombinant host cell of claim 12, wherein the hyaluronan synthase protein comprises a central intracellular domain, at least two transmembrane domains at an amino end thereof, and at least two membrane-associated domains at a carboxyl end thereof.

16. A recombinant host cell comprising at least one expression construct comprising:
  a hyaluronan synthase gene, wherein the hyaluronan synthase gene encodes a single protein that is a dual-action catalyst that utilizes UDP-GlcA and UDP-GlcNAc to synthesize HA;
  at least one gene encoding an enzyme for synthesis of a hyaluronic acid sugar precursor; and
  wherein the recombinant host cell produces HA.

17. The recombinant host cell of claim 16, wherein the hyaluronan synthase gene is isolated from a streptococcal source.

18. The recombinant host cell of claim 16, wherein the hyaluronan synthase gene is isolated from a microorganism.

19. The recombinant host cell of claim 16, wherein the enzyme for synthesis of a hyaluronic acid sugar precursor is selected from the group consisting of a pyrophosphorylase, a transferase, a mutase, a dehydrogenase, or an epimerase, capable of producing UDP-GlcNAc or UDP-GlcUA.

20. The recombinant host cell of claim 16, wherein the hyaluronan synthase protein comprises a central intracellular domain, at least two transmembrane domains at an amino end thereof, and at least two membrane-associated domains at a carboxyl end thereof.

* * * * *

UNITED STATES PATENT AND TRADEMARK OFFICE
CERTIFICATE OF CORRECTION

PATENT NO. : 7,060,466 B2
APPLICATION NO. : 11/109855
DATED : June 13, 2006
INVENTOR(S) : Paul H. Weigel et al.

It is certified that error appears in the above-identified patent and that said Letters Patent is hereby corrected as shown below:

Column 2, line 5: After the words "Groups A and C" delete word "Stereptococci" and replace with the word --Streptococci--.

Column 2, line 10: After the word "that" delete the word "Stereptococci" and replace with the word --Streptococci--.

Column 4, line 4: Delete "Xenopuslaevis" and replace with the words --Xenopus laevis--.

Column 6, line 41: After the number "588", delete "(XHAS)" and replace with --(XlHAS)--

Column 7, line 17: Delete the word "Stereptococci" and replace with the word --Streptococci--.

Column 7, line 61: Delete "($H_{\Delta size}$)" and replace with --($HA_{\Delta size}$)--.

Column 7, line 61: Delete "($H_{\Delta mod}$)" and replace with --($HA_{\Delta mod}$)--.

Column 13, line 67: After "(i)" and before "and Val;" delete "lie" and replace with --Ile--.

Column 18, line 39: Delete the symbol "$\geqq$" and replace with the symbol -- $\geq$ --.

Column 19, line 64: Delete "[Paramecium bursaria chlorella virus]" and replace with --[Paramecium bursaria chlorella virus]--.

Column 29, line 14: Delete "Bi833-741" and replace with --Bi8337-41--.

Column 29, line 31: Delete the word "Stereptococci" and replace with the word --Streptococci--.

Column 31, line 16: Delete "mgaane" and replace with --mg/lane--.

Column 31, line 34: After "UDP-" and before "in vitro" delete "Gla" and replace with --GlcA--.

Column 31, line 66: After "predigested" and before "Zap" delete "A" and replace with the symbol --$\lambda$--.

UNITED STATES PATENT AND TRADEMARK OFFICE
CERTIFICATE OF CORRECTION

PATENT NO. : 7,060,466 B2
APPLICATION NO. : 11/109855
DATED : June 13, 2006
INVENTOR(S) : Paul H. Weigel et al.

It is certified that error appears in the above-identified patent and that said Letters Patent is hereby corrected as shown below:

Column 32, line 20: After "ACX" and before "TAY" delete "MT" and replace with --AAT--.

Column 32, line 55: After "TWT" and before "GAR" delete "MY" and replace with --AAY--.

Column 36, line 25: Delete the symbol "$\leqq$" and replace with the symbol --$\leq$--.

Column 36, line 63: Delete "Mr" and replace --$M_r$--.

Column 37, line 21: Delete the symbol "$\leqq$" and replace with the symbol --$\leq$--.

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,060,466 B2 Page 1 of 1
APPLICATION NO. : 11/109855
DATED : June 13, 2006
INVENTOR(S) : Paul H. Weigel, Paul L. DeAngelis and Kshama Kumari It is certified that error appears in the above-identified patent and that said Letters Patent is hereby corrected as shown below:

Column 1, lines 27-29: should read as follows: -- This invention was made with government support under Contract Number GM035978 awarded by the National Institutes of Health. The government has certain rights in the invention. --

Signed and Sealed this

Twenty-first Day of September, 2010

David J. Kappos
*Director of the United States Patent and Trademark Office*